United States Patent
Delanghe et al.

(10) Patent No.: US 12,171,811 B2
(45) Date of Patent: Dec. 24, 2024

(54) COMPOSITIONS FOR USE TO TREAT ADVANCED GLYCATION END PRODUCTS-DEPENDENT OCULAR DISEASES

(71) Applicant: Universiteit Gent, Ghent (BE)

(72) Inventors: Joris Delanghe, Aalst (BE); Elisabeth Van Aken, Heusden (BE)

(73) Assignee: Universiteit Gent, Ghent (BE)

( * ) Notice: Subject to any disclaimer, the term of this patent is extended or adjusted under 35 U.S.C. 154(b) by 801 days.

(21) Appl. No.: 17/269,234

(22) PCT Filed: Sep. 10, 2019

(86) PCT No.: PCT/EP2019/074058
§ 371 (c)(1),
(2) Date: Feb. 17, 2021

(87) PCT Pub. No.: WO2020/053188
PCT Pub. Date: Mar. 19, 2020

(65) Prior Publication Data
US 2021/0322523 A1 Oct. 21, 2021

(30) Foreign Application Priority Data

Sep. 14, 2018 (EP) .................................... 18194420
Jul. 8, 2019 (EP) .................................... 19184875

(51) Int. Cl.
| | | |
|---|---|---|
| A61K 38/45 | (2006.01) |
| A61K 9/00 | (2006.01) |
| A61K 31/7076 | (2006.01) |
| A61K 33/06 | (2006.01) |
| A61K 47/20 | (2006.01) |
| A61K 47/42 | (2017.01) |
| A61P 3/10 | (2006.01) |
| A61P 27/02 | (2006.01) |
| C12N 9/12 | (2006.01) |

(52) U.S. Cl.
CPC ............ *A61K 38/45* (2013.01); *A61K 9/0019* (2013.01); *A61K 9/0048* (2013.01); *A61K 31/7076* (2013.01); *A61K 33/06* (2013.01); *A61K 47/20* (2013.01); *A61K 47/42* (2013.01); *A61P 3/10* (2018.01); *A61P 27/02* (2018.01); *C12N 9/1205* (2013.01); *C12Y 207/01171* (2013.01)

(58) Field of Classification Search
CPC .... A61K 38/45; A61K 9/0019; A61K 9/0048; A61K 31/7076; A61K 33/06; A61K 47/20; A61K 47/42; A61P 3/10; A61P 27/02; C12N 9/1205; C12Y 207/01171
See application file for complete search history.

(56) References Cited

FOREIGN PATENT DOCUMENTS

WO 2007/117394 A2 10/2007
WO 2019/149648 A1 8/2019

OTHER PUBLICATIONS

Delpierre, et al., Biochem J. Aug. 1, 2002;365(Pt 3):801-808. doi: 10.1042/BJ20020325. PMID: 11975663; PMCID: PMC1222720. (Year: 2002).*
Kandarakis SA, Piperi C, Topouzis F, Papavassiliou AG. Emerging role of advanced glycation-end products (AGEs) in the pathobiology of eye diseases. Prog Retin Eye Res. Sep. 2014;42:85-102. doi: 10.1016/j.preteyeres.2014.05.002. Epub Jun. 4, 2014. PMID: 24905859. (Year: 2014).*
Kishabongo AS, Katchunga P, Cikomola JC, De Somer FM, De Buyzere ML, Speeckaert MM, Delanghe JR. The presence of fructosamine in human aortic valves is associated with valve stiffness. J Clin Pathol. Sep. 2016;69(9):772-6. doi: 10.1136/jclinpath-2015-203409. Epub Feb. 5, 2016. PMID: 26850632. (Year: 2016).*
Ahmad M, Hirz M, Pichler H, Schwab H. Protein expression in Pichia pastoris: recent achievements and perspectives for heterologous protein production. Appl Microbiol Biotechnol. Jun. 2014;98(12):5301-17. doi: 10.1007/s00253-014-5732-5. Epub Apr. 1, 20148. PMID: 24743983; PMCID: PMC4047484. (Year: 2014).*
SCORE Sequence search results run on on Jan. 18, 2024, 8 pages of PDF. (Year: 2024).*
Andexer et al. "Emerging Enzymes for ATP Regeneration in Biocatalytic Processes" ChemBioChem 16: 380-386 (Feb. 2015).

(Continued)

*Primary Examiner* — Kade Ariani
(74) *Attorney, Agent, or Firm* — TraskBritt

(57) ABSTRACT

The disclosure relates to the treatment of blindness due to age-related presbyopia, age-related macular degeneration (AMD), diabetic retinopathy (DR) and/or diabetic macular edema (DME) in a human or animal. Age-related presbyopia is the loss of accommodation in any individual more than 40-50 years old, currently treated by reading glasses. AMD is the most common cause of irreversible loss of sight in persons >65 years in the western world. At this time, no treatment is available for the dry form of AMD. The dry form of AMD is characterized by vision threatening Drüsen, which are (sub)retinal accumulations of advanced glycation end products (AGEs) and fluorophores. DR and DME are the most common cause of irreversible loss of sight in persons <65 years in the western world. Current therapies for age-related presbyopia, AMD, DR and DME are disappointing and do not prevent the evolution to vision impairment, atrophy or blindness. The disclosure specifically relates to the administration of fructosamine-3-kinase and its cofactor(s). This results in deglycation and inactivation of AGEs and fluorophores.

13 Claims, 20 Drawing Sheets
Specification includes a Sequence Listing.

(56) References Cited

OTHER PUBLICATIONS

Ausubel et al. "Current Protocols in Molecular Biology" (supplement 114), John Wiley & Sons, New York (Apr. 2016).
Bejarano et al. "Too sweet: problems of protein glycation in the eye" Exp Eye Res; 178:255-262 (Jan. 2019).
Bergen et al. "On the origin of proteins in human drusen: The meet, greet and stick hypothesis" Prog Retin Eye Res; 70:55-84 (May 2019).
Bogunovic et al. "Machine learning of the progression of intermediated age-related macular degeneration based on OCT imaging" IOVS, Vo. 58 No. 6, Bio141-150 (Jul. 2017).
Cheng et al. "Overview of clinical trials for dry age-related macular degeneration" J Med Sci; 37:121-9 (May 2017).
Claes et al. "Modular Integrated Secretory System Engineering in Pichia Pastoris To Enhance G-Protein Coupled Receptor Expression" ACS Synthetic Biology 5, (10) (May 2016): 1070-75.
Delpierre et al. "Fructosamine 3-kinase is involved in an intracellular deglycation pathway in human erythrocytes" Biochem J 365:801-8 (Feb. 2002).
Delpierre et al. "Identification, cloning, and heterologous expression of a mammalian fructosamine-3-kinase" Diabetes 49: 1627-1634 (Oct. 2000).
Dunmore et al. "Evidence That Differences in Fructosamine-3-Kinase Activity May Be Associated With the Glycation Gap in Human Diabetes" Diabetes (Jan. 2018) 67:131-136 | https://doi.org/10.2337/db17-0441.
Glenn et al. "The role of advanced glycation end products in retinal ageing and disease" Biochim Biophys Acta (Oct. 2009) 1790:1109-1116.
Halfter et al. "Embryonic synthesis of the inner limiting membrane and vitreous body" Invest Ophthalmol Vis Sci (Jun. 2005);46:2202-9.
Hollyfield et al. Proteomic Approaches to Understanding Age-Related Macular Degeneration: Retinal Degenerations. Advances in Experimental Medicine and Biology, vol. 533. Springer, Boston, MA . (2003) Accessed Feb. 2021 https://doi.org/10.1007/978-1-4615-0067-4_11.
International Search Report for International Application No. PCT/EP2019/074058, mailed Jan. 8, 2020, 5 pages.
International Written Opinion for International Application No. PCT/EP2019/074058, mailed Jan. 8, 2020, 7 pages.
Matthews et al. "Risks of progression of retinopathy and vision loss related to tight blood pressure control in type 2 diabetes mellitus: UKPDS 69" Arch Ophthalmol (Nov. 2004) 122(11): 1631-40.
Moon et al. Effects of ATP regeneration systems on the yields and solubilities of cell-free synthesized protein: Journal of Industrial and Engineering Chemistry, vol. 70, pp. 276-280 (Feb. 2019).
Rosenfeld et al. "Ranibizumab for neovascular age-related macular degeneration" N Engl J Med (Oct. 2006) 355(14):1419-31.
Sambrook et al. Molecular Cloning: A laboratory Manual, 4th ed., Cold Spring Harbor press, Plainsview, New York (Jun. 2012).
Stitt "The Maillard Reaction in Eye Diseases" Ann N Y Acad Sci (Jun. 2005) 1043:582-597.
Szwergold et al. "Human fructosamine-3-Kinase: Purification, Sequencing, Substrate Specificity, And Evidence Of Activity In Vivo" Diabetes (Sep. 2001) 50(9): 2139-2147.
Van Schaftinger et al. "Enzymatic repair of Amadori Products" Amino Acids 42, 1143-1150 (Oct. 2010).
Wang et al. "Photosensitization of A2E triggers telomere dysfunction and accelerates retinal pigment epithelium senescence" Cell Death and Disease (Feb. 2018) 9(2):178.
White et al. "Beneficial effects of intensive therapy of diabetes during adolescence: outcomes after the conclusion of the Diabetes Control and Complications Trial (DCCT)" J Pediat (Dec. 2001) 139:804-812.
Wong et al. "Global prevalence of age-related macular degeneration and disease burden projection for 2020 and 2040: A systematic review and meta-analysis" Lancet Glob Health (Feb. 2014) 2(2):e106-16.
Woodyer et al. "Regeneration of Cofactors for Enzyme Biocatalysis in Enzyme Technology," in Enzyme Technology; 19 pages (Springer Science+Business Media, Inc. and Asiatech Publishers, Inc., (Jan. 2006).
Yamada et al. "The expression of advanced glycation endproduct receptors in RPE cells associated with basal deposits in human maculas" Exp Eye Res (May 2006) 82(5):840-848.
Yoon et al. "A Novel Source of Methylglyoxal and Glyoxal in Retina: Implications For Age-Related Macular Degeneration" PLoS One (Jul. 2012) 7(7): e41309.
De Bruyne et al. "Fructosamine-3-Kinase as a Potential Treatment Option for Age-Related Macular Degeneration" J Clin Med. Sep. 4, 2020;9(9):2869. doi: 10.3390/jcm9092869. PMID: 32899850; PMCID: PMC7565857.
De Bruyne et al. "A Potential Role for Fructosamine-3-Kinase in Cataract Treatment" Int J Mol Sci. Apr. 7, 2021;22(8):3841. doi: 10.3390/ijms22083841. PMID: 33917258; PMCID: PMC8068021.
Delanghe et al. "Fructosyl Amino Oxidase as a Therapeutic Enzyme in Age-Related Macular Degeneration" Int. J. Mol. Sci. 25, 4779 (2024). https://doi.org/10.3390/ijms25094779.
Delanghe et al. "Topical application of deglycating enzymes as an alternative non-invasive treatment for presbyopia" Int J Mol Sci 2023;24(8):7343. doi 10.3390/ijms087343.
Krishnamurthy et al. "The Role of Proteoglycans and Glycosaminoglycans in Heart Valve B" Advances in Heart Valve Biomechanics, pp. 59-79 (Jan. 2018); doi: 10.1007/978-3-030-01993-8_3.
Minnaert et al. "Yeast-produced fructosamine-3-kinase retains mobility after intravitreal injection and topical application in human and bovine eyes as determined by fluorescence correlation spectroscopy" Int J Pharmaceutics 2022; 621: 121772 doi: 10.1016/j.ijpharm.2022.121772.

* cited by examiner

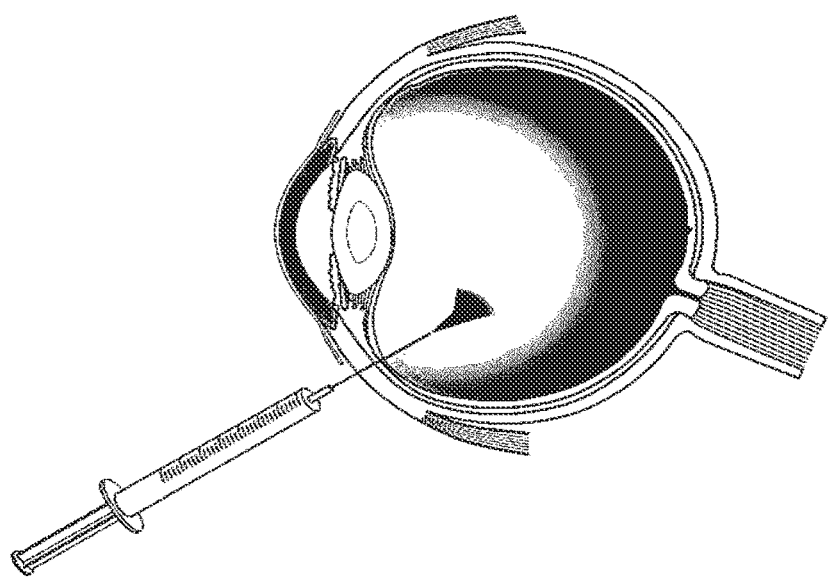
FIG. 1 scheme of the proposed procedure

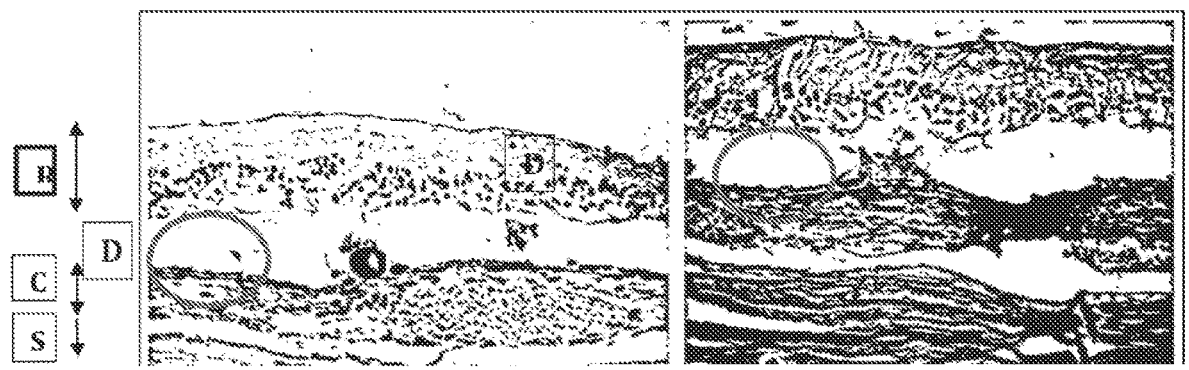
FIG. 2A saline treated Drüse  FIG. 2B FN3K treated Drüse (magnification x200)
R retina, C choroid, S sclera, D encircled Drüse Light microscopy          RGB colour
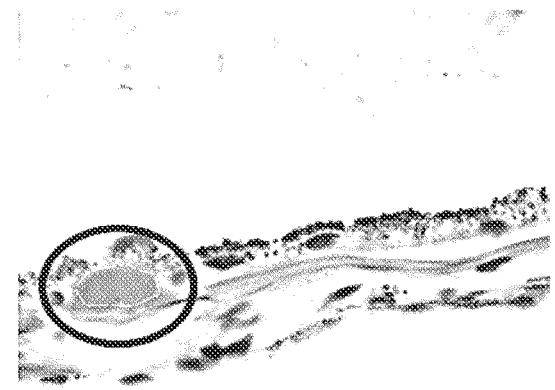
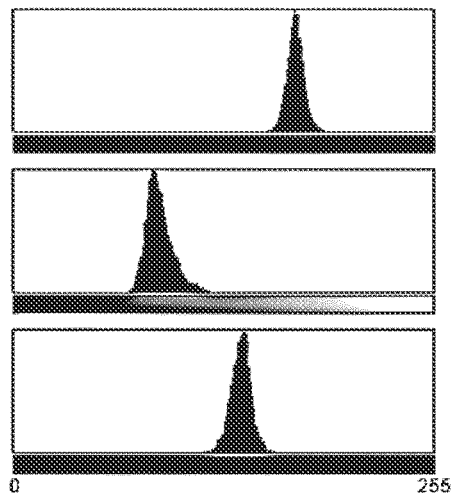
Saline treated
Count: 14545
rMean: 171.42   rSD: 5.48    rMode: 171
gMean: 88.47    gSD: 8.50    gMode: 84
bMean: 137.94   bSD: 6.63    bMode: 140
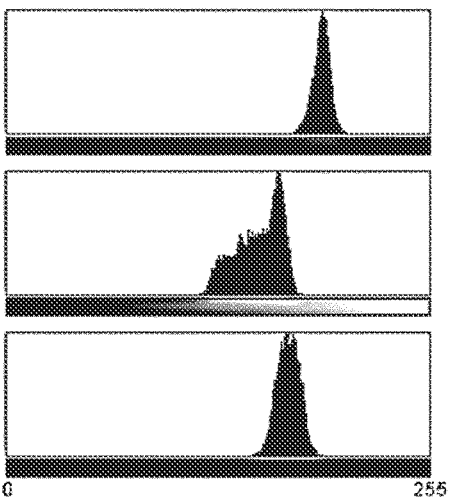
Fn3K treated
Count: 16287
rMean: 190.19   rSD: 5.37    rMode: 191
gMean: 152.06   gSD: 13.91   gMode: 164
bMean: 170.06   bSD: 7.14    bMode: 173
FIG. 2C

Fn3K treated Drüsen
Saline treated Drüsen
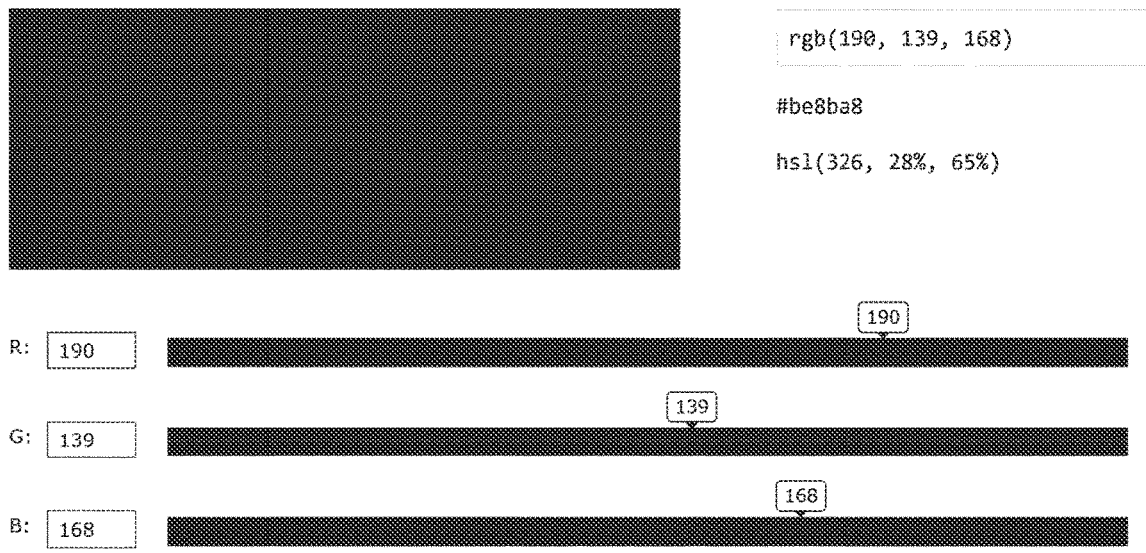
FIG. 2D

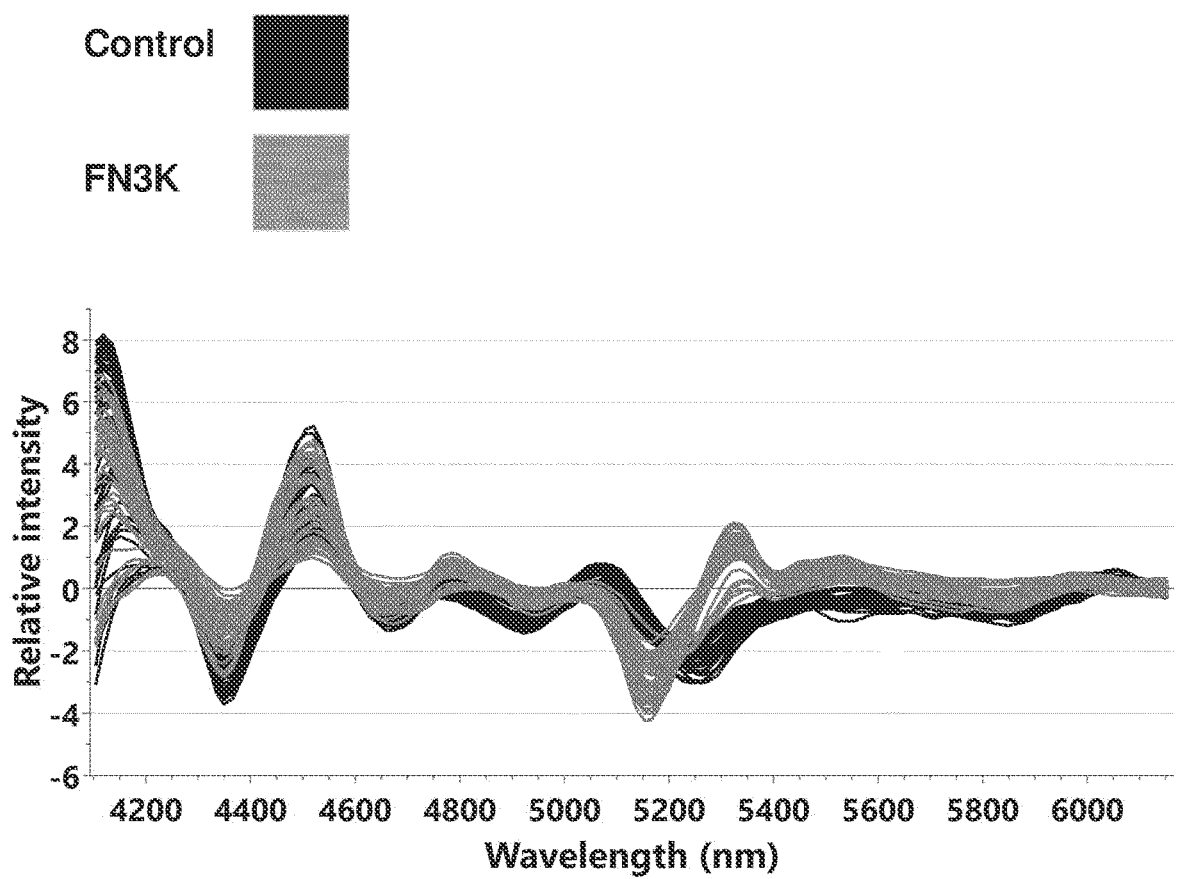
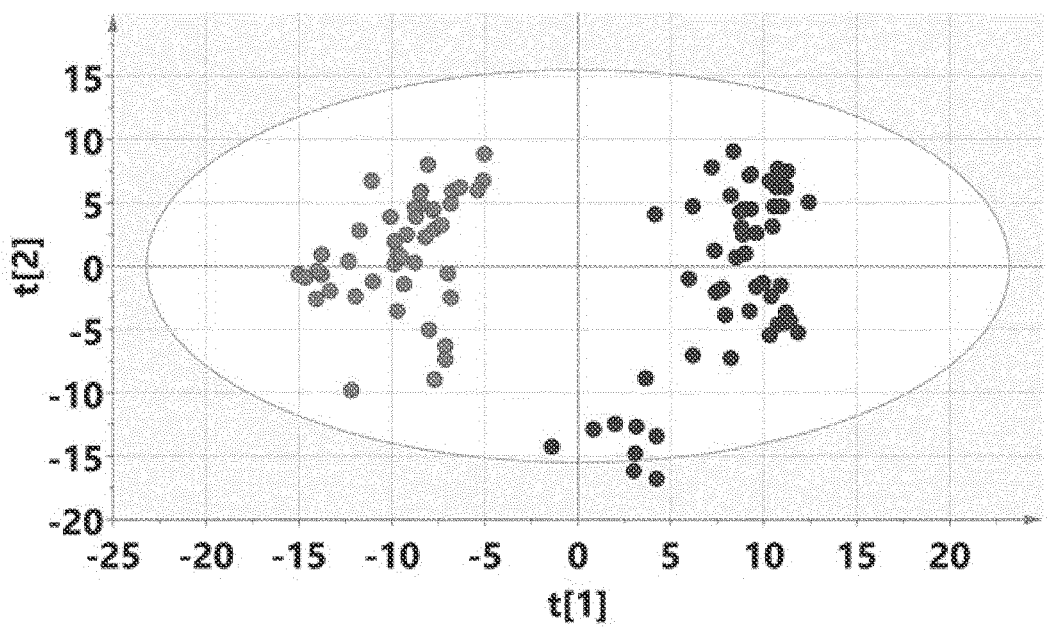
FIG. 3B Bruch's membrane

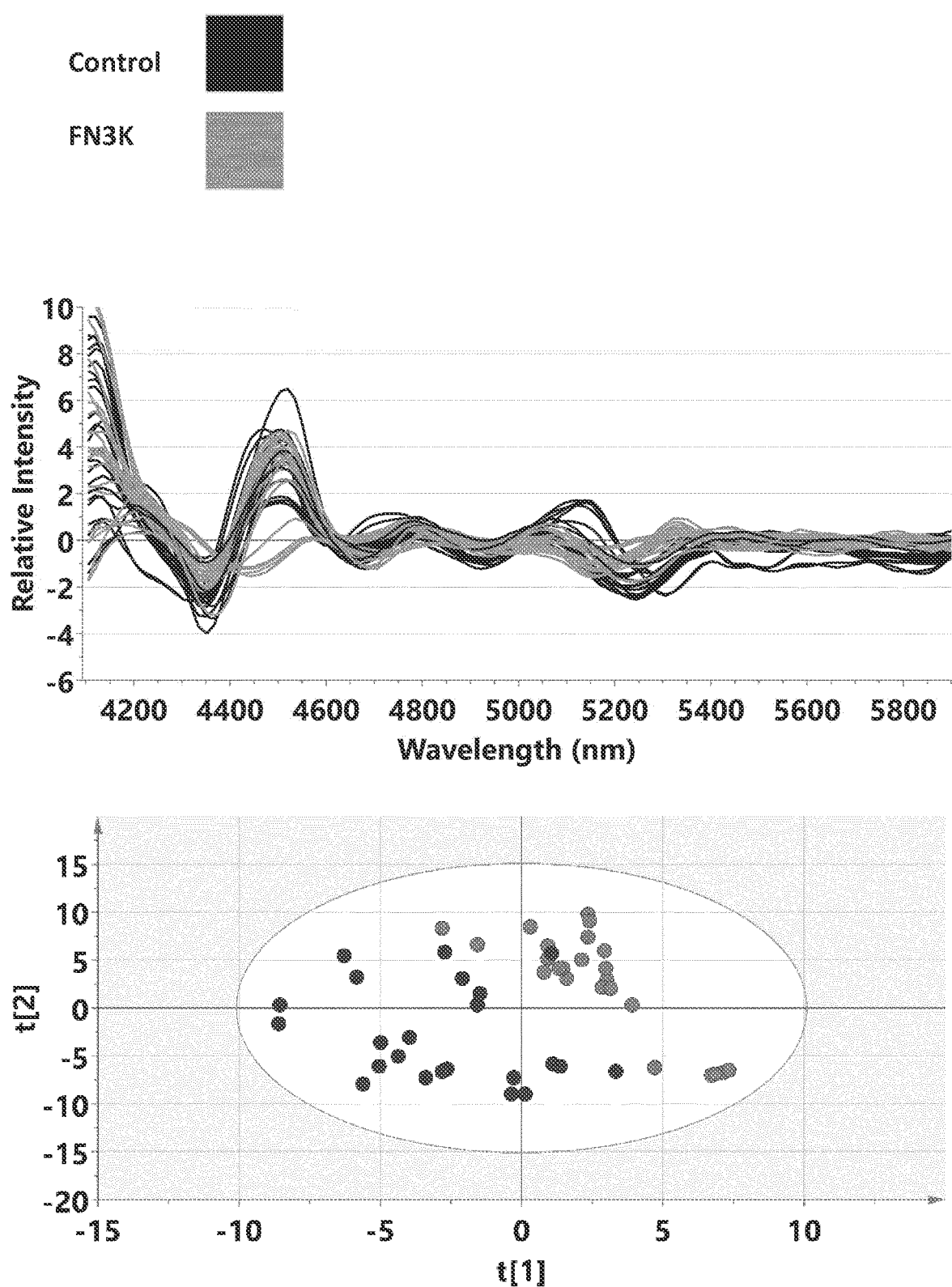
FIG. 3C Subretinal Drüsen

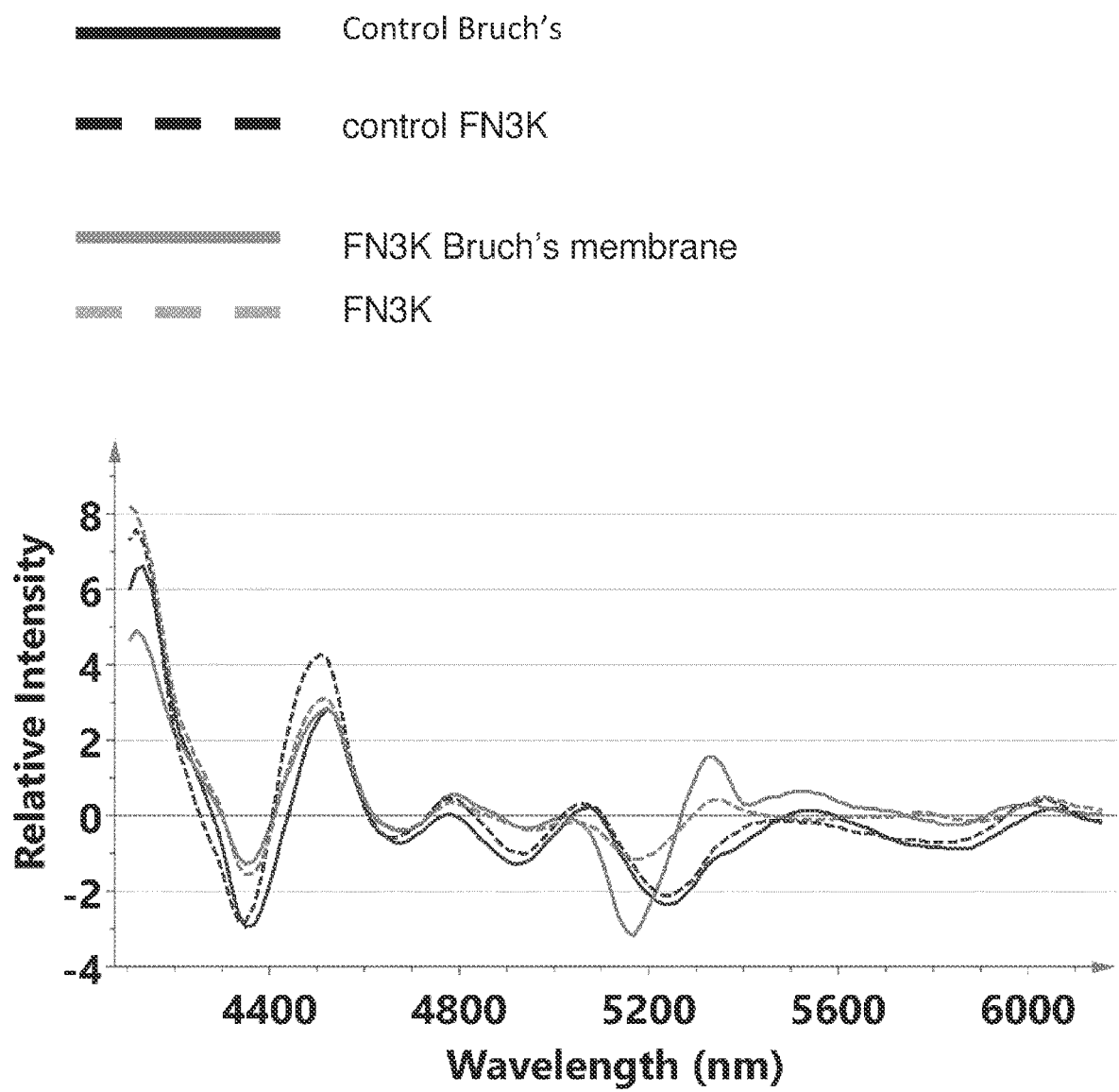
FIG. 3D Mean

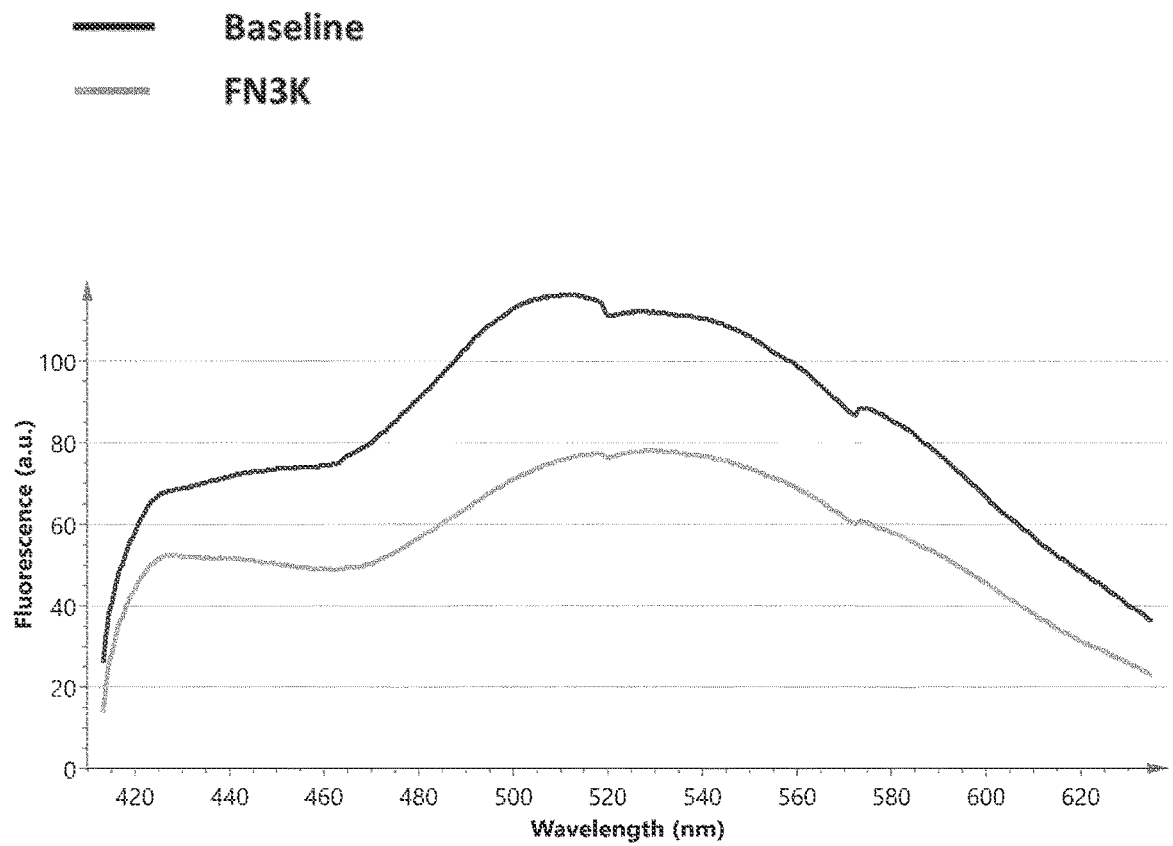
FIG. 4B1

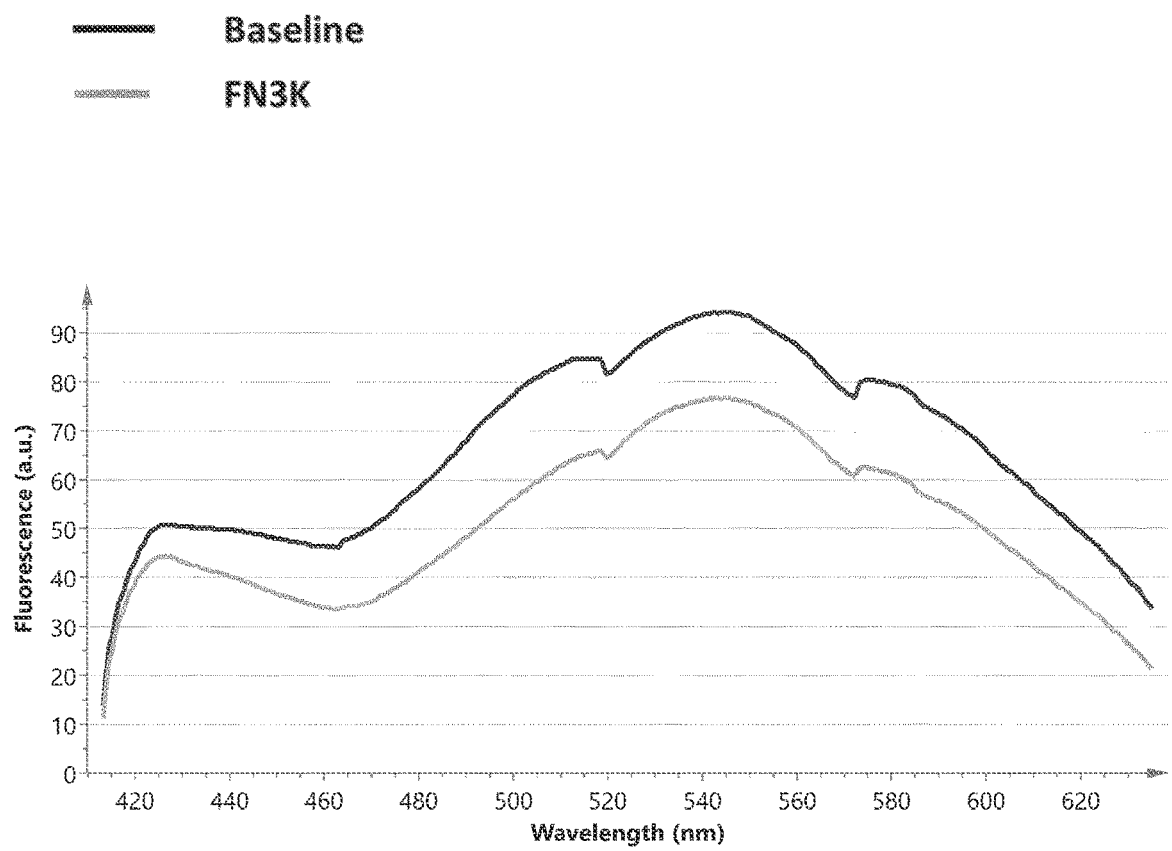
FIG. 4B2

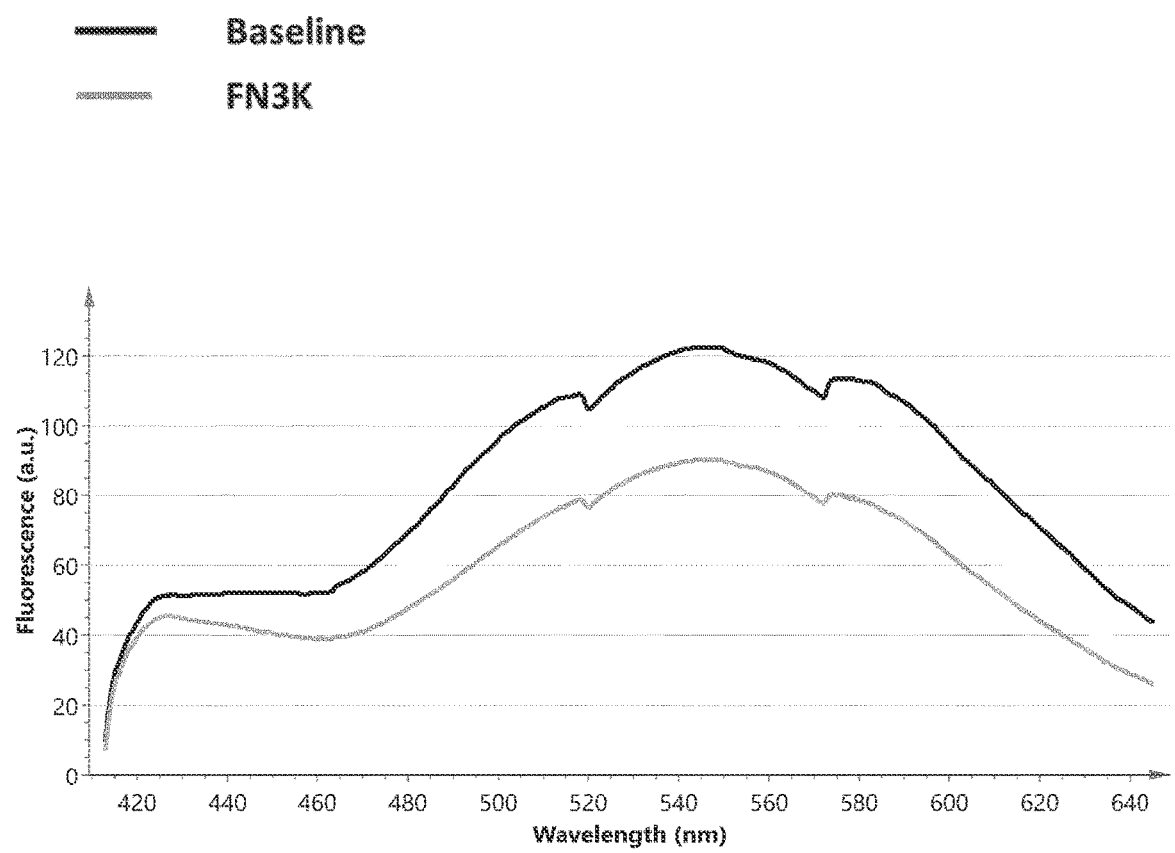
FIG. 4B3

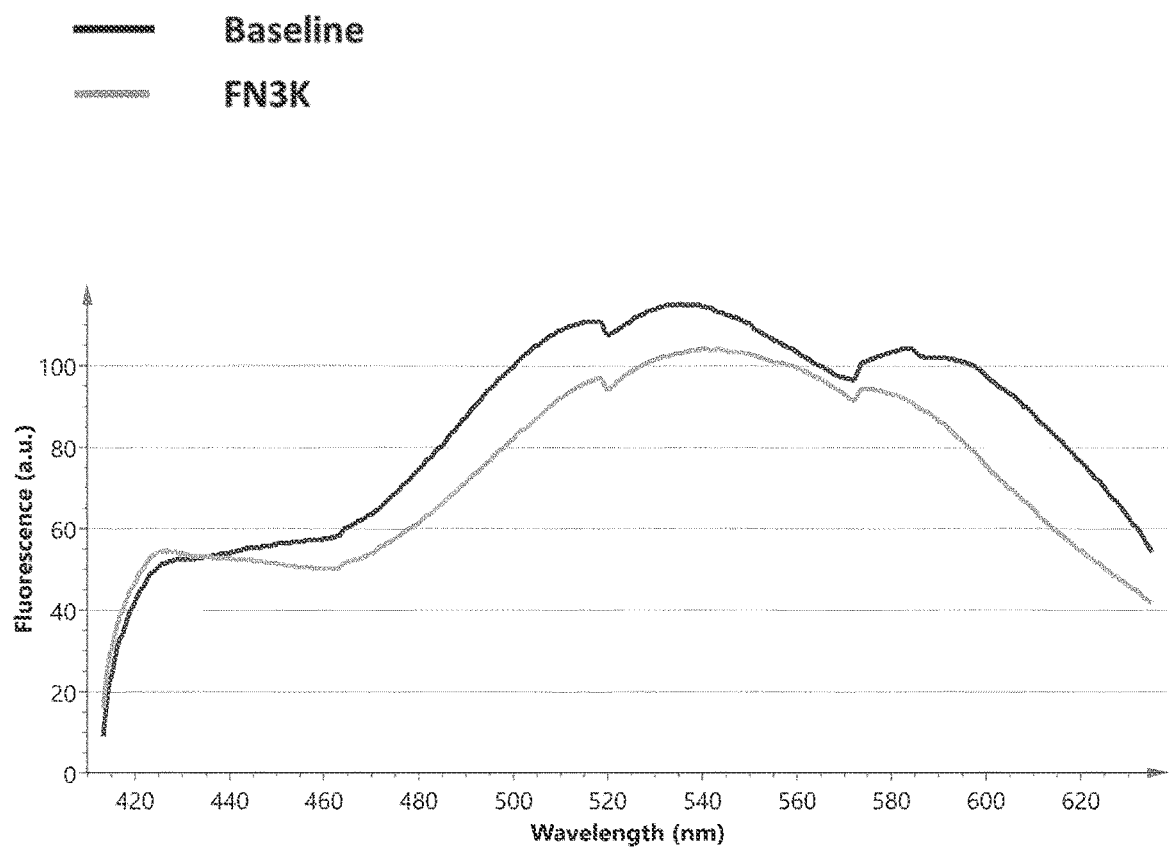
FIG. 4B4

Mouse 1 saline treated                Fn3K treated
Mouse 2 saline treated    Fn3K treated
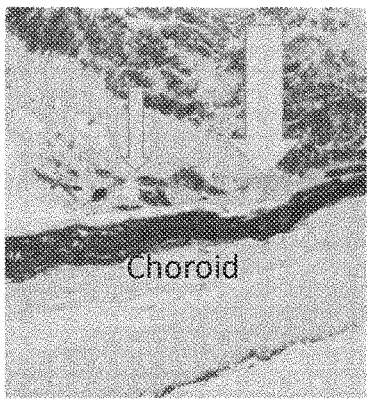
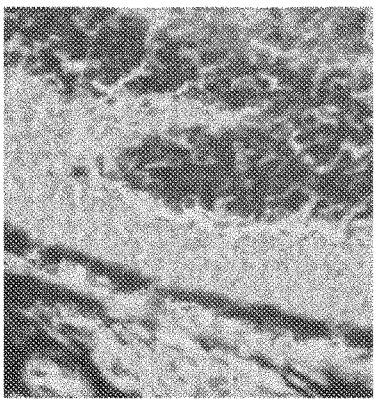
FIG. 5

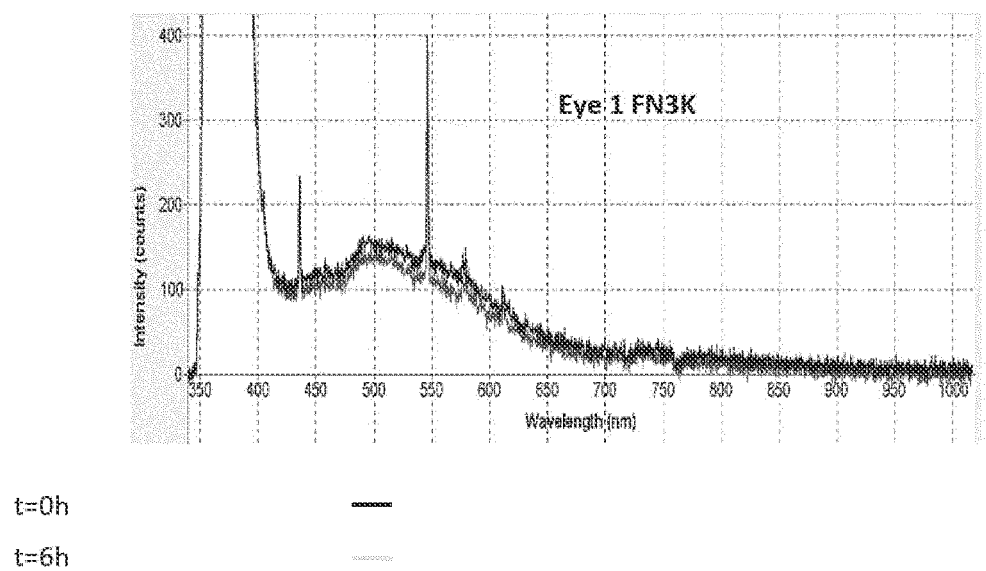
t=0h
t=6h
FIG. 9B1
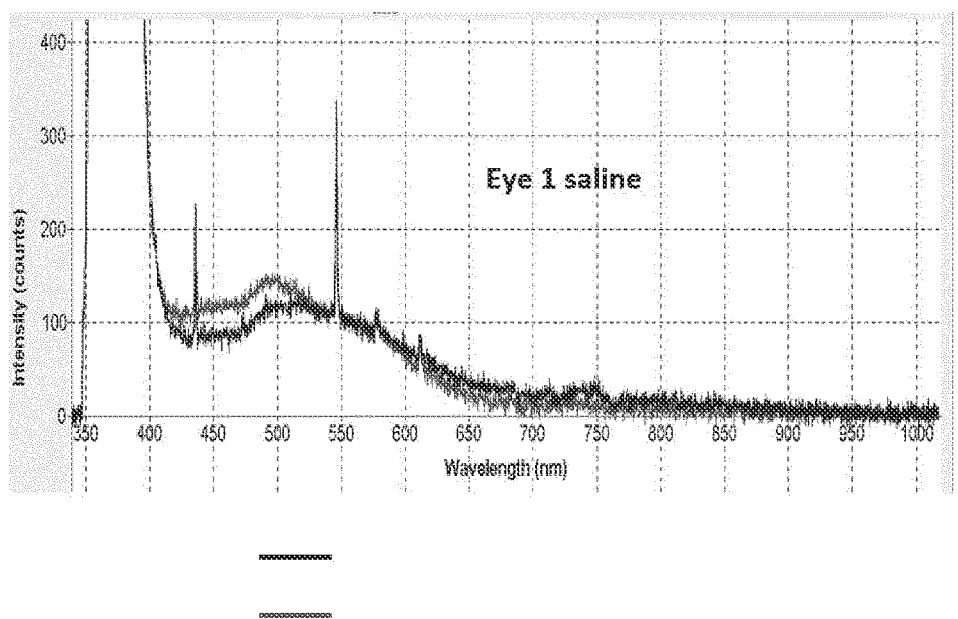
t=6h
t=12h
FIG. 9B2

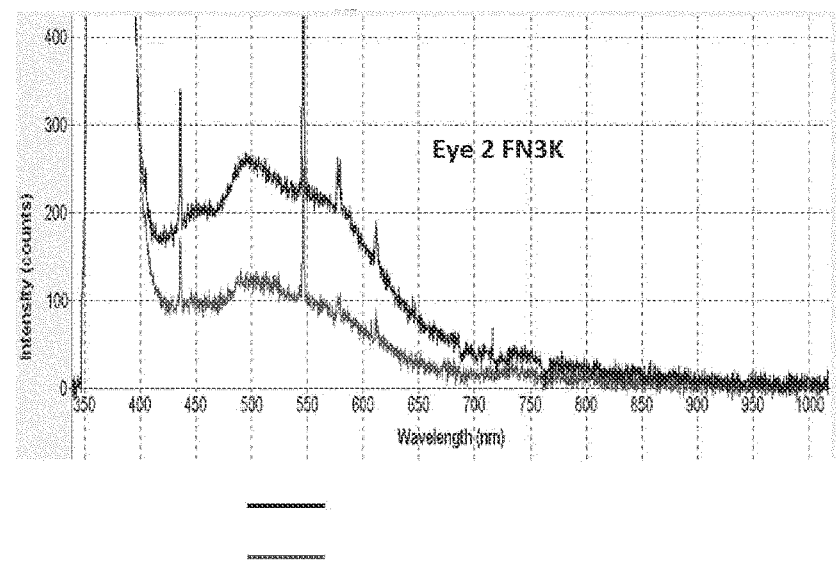
t=6h
t=12h
FIG. 9B3
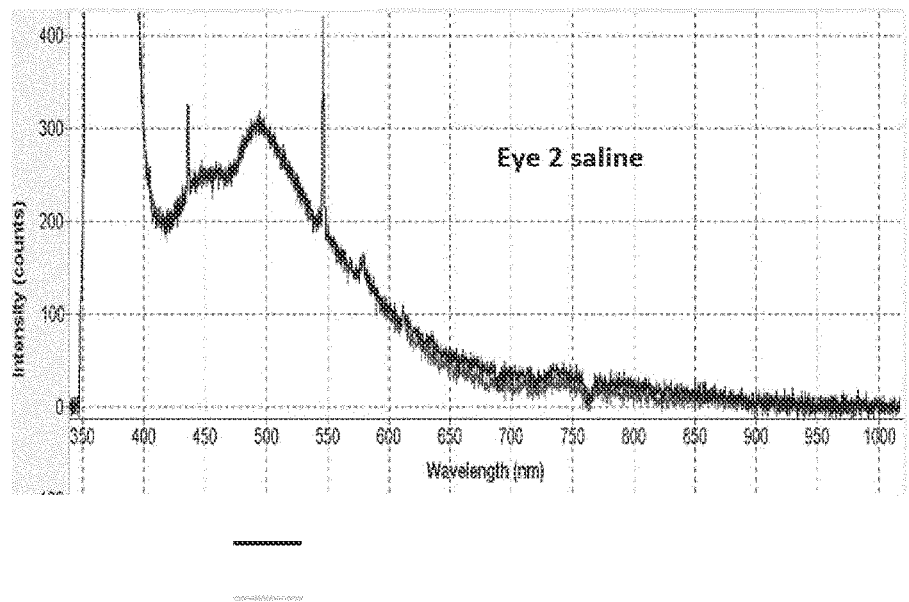
t=0h
t=6h
FIG. 9B4

SEQUENCE LISTING

<160> NUMBER OF SEQ ID NOS: 4

<210> SEQ ID NO 1
<211> LENGTH: 325
<212> TYPE: PRT
<213> ORGANISM: Homo sapiens

<400> SEQUENCE: 1

Met His His His His His Val Asn Gly Pro Gly Ser Asp Glu Val
1               5                   10                  15

Asp Glu Gln Leu Leu Arg Ala Glu Leu Arg Thr Ala Thr Leu Arg Ala
                20                  25                  30

Phe Gly Gly Pro Gly Ala Gly Cys Ile Ser Glu Gly Arg Ala Tyr Asp
            35                  40                  45

Thr Asp Ala Gly Pro Val Phe Val Lys Val Asn Arg Arg Thr Gln Ala
    50                  55                  60

Arg Gln Met Phe Glu Gly Glu Val Ala Ser Leu Glu Ala Leu Arg Ser
65                  70                  75                  80

Thr Gly Leu Val Arg Val Pro Arg Pro Met Lys Val Ile Asp Leu Pro
                85                  90                  95

Gly Gly Gly Ala Ala Phe Val Met Glu His Leu Lys Met Lys Ser Leu
            100                 105                 110

Ser Ser Gln Ala Ser Lys Leu Gly Glu Gln Met Ala Asp Leu His Leu
        115                 120                 125

Tyr Asn Gln Lys Leu Arg Glu Lys Leu Lys Glu Glu Asn Thr Val
    130                 135                 140

Gly Arg Arg Gly Glu Gly Ala Glu Pro Gln Tyr Val Asp Lys Phe Gly
145                 150                 155                 160

Phe His Thr Val Thr Cys Cys Gly Phe Ile Pro Gln Val Asn Glu Trp
                165                 170                 175

Gln Asp Asp Trp Pro Thr Phe Phe Ala Arg His Arg Leu Gln Ala Gln
            180                 185                 190

Leu Asp Leu Ile Glu Lys Asp Tyr Ala Asp Arg Glu Ala Arg Glu Leu
        195                 200                 205

Trp Ser Arg Leu Gln Val Lys Ile Pro Asp Leu Phe Cys Gly Leu Glu
    210                 215                 220

Ile Val Pro Ala Leu Leu His Gly Asp Leu Trp Ser Gly Asn Val Ala
225                 230                 235                 240

Glu Asp Asp Val Gly Pro Ile Ile Tyr Asp Pro Ala Ser Phe Tyr Gly
                245                 250                 255

His Ser Glu Phe Glu Leu Ala Ile Ala Leu Met Phe Gly Gly Phe Pro
            260                 265                 270

Arg Ser Phe Phe Thr Ala Tyr His Arg Lys Ile Pro Lys Ala Pro Gly
        275                 280                 285

Phe Asp Gln Arg Leu Leu Leu Tyr Gln Leu Phe Asn Tyr Leu Asn His
    290                 295                 300

Trp Asn His Phe Gly Arg Glu Tyr Arg Ser Pro Ser Leu Gly Thr Met

```
                305                 310                 315                 320
Arg Arg Leu Leu Lys
            325

<210> SEQ ID NO 2
<211> LENGTH: 308
<212> TYPE: PRT
<213> ORGANISM: Homo sapiens

<400> SEQUENCE: 2

Glu Gln Leu Leu Arg Ala Glu Leu Arg Thr Ala Thr Leu Arg Ala Phe
1               5                   10                  15

Gly Gly Pro Gly Ala Gly Cys Ile Ser Glu Gly Arg Ala Tyr Asp Thr
            20                  25                  30

Asp Ala Gly Pro Val Phe Val Lys Val Asn Arg Arg Thr Gln Ala Arg
        35                  40                  45

Gln Met Phe Glu Gly Glu Val Ala Ser Leu Glu Ala Leu Arg Ser Thr
    50                  55                  60

Gly Leu Val Arg Val Pro Arg Pro Met Lys Val Ile Asp Leu Pro Gly
65                  70                  75                  80

Gly Gly Ala Ala Phe Val Met Glu His Leu Lys Met Lys Ser Leu Ser
            85                  90                  95

Ser Gln Ala Ser Lys Leu Gly Glu Gln Met Ala Asp Leu His Leu Tyr
        100                 105                 110

Asn Gln Lys Leu Arg Glu Lys Leu Lys Glu Glu Asn Thr Val Gly
    115                 120                 125

Arg Arg Gly Glu Gly Ala Glu Pro Gln Tyr Val Asp Lys Phe Gly Phe
130                 135                 140

His Thr Val Thr Cys Cys Gly Phe Ile Pro Gln Val Asn Glu Trp Gln
145                 150                 155                 160

Asp Asp Trp Pro Thr Phe Phe Ala Arg His Arg Leu Gln Ala Gln Leu
            165                 170                 175

Asp Leu Ile Glu Lys Asp Tyr Ala Asp Arg Glu Ala Arg Glu Leu Trp
        180                 185                 190

Ser Arg Leu Gln Val Lys Ile Pro Asp Leu Phe Cys Gly Leu Glu Ile
    195                 200                 205

Val Pro Ala Leu Leu His Gly Asp Leu Trp Ser Gly Asn Val Ala Glu
210                 215                 220

Asp Asp Val Gly Pro Ile Ile Tyr Asp Pro Ala Ser Phe Tyr Gly His
225                 230                 235                 240

Ser Glu Phe Glu Leu Ala Ile Ala Leu Met Phe Gly Gly Phe Pro Arg
            245                 250                 255

Ser Phe Phe Thr Ala Tyr His Arg Lys Ile Pro Lys Ala Pro Gly Phe
        260                 265                 270

Asp Gln Arg Leu Leu Leu Tyr Gln Leu Phe Asn Tyr Leu Asn His Trp
    275                 280                 285

Asn His Phe Gly Arg Glu Tyr Arg Ser Pro Ser Leu Gly Thr Met Arg
290                 295                 300

Arg Leu Leu Lys
305

<210> SEQ ID NO 3
<211> LENGTH: 978
<212> TYPE: DNA
<213> ORGANISM: Homo sapiens
```

<400> SEQUENCE: 3

```
atgcatcatc atcatcatca tgttaacggt ccaggttctg atgaagttga tgaacagttg      60
ttgagagctg agttgagaac tgctactttg agagctttg gtggtccagg tgctggttgt     120
atttctgagg gtagagctta cgatactgac gctggtccag ttttcgttaa ggttaacaga    180
agaactcagg ctagacagat gttcgagggt gaagttgctt ctttggaggc tttgagatcc    240
actggttttgg ttagagttcc aagaccaatg aaggttatcg acttgccagg tggtggtgct   300
gcttttgtta tggaacactt gaagatgaag tccttgtcct cccaggcttc taagttgggt    360
gaacaaatgg ctgacttgca cttgtacaac cagaagttga gagaaaagtt gaaagaggaa    420
gagaacactg ttggtagaag aggtgaaggt gctgagccac aatacgttga caagttcggt    480
ttccacactg ttacttgttg tggtttcatc ccacaggtta acgagtggca agatgactgg    540
ccaactttct cgctagaca cagattgcaa gctcagttgg acttgatcga aggactac      600
gctgacagag aagctagaga attgtggtcc agattgcagg ttaagatccc agacttgttc    660
tgtggtttgg agatcgttcc agctttgttg cacggtgatt tgtggtctgg taacgttgct    720
gaagatgacg ttggtccaat tatctacgac ccagcttctt tctacggtca ctctgaattc    780
gagttggcta tcgctttgat gttcggtggt ttcccaagat ccttcttcac tgcttaccac    840
agaaagatcc caaaggctcc aggttttcgac cagagattgt tgttgtacca gttgttcaac    900
tacttgaacc attggaacca cttcggtaga gagtacagat ctccatcctt gggtactatg    960
agaagattgt tgaagtaa                                                   978
```

<210> SEQ ID NO 4
<211> LENGTH: 927
<212> TYPE: DNA
<213> ORGANISM: Homo sapiens

<400> SEQUENCE: 4

```
gaacagttgt tgagagctga gttgagaact gctactttga gagcttttgg tggtccaggt     60
gctggttgta tttctgaggg tagagcttac gatactgacg ctggtccagt tttcgttaag    120
gttaacagaa gaactcaggc tagacagatg ttcgagggtg aagttgcttc tttggaggct    180
ttgagatcca ctggttttgg tagagttcca agaccaatga aggttatcga cttgccaggt    240
ggtggtgctg cttttgttat ggaacacttg aagatgaagt ccttgtcctc ccaggcttct    300
aagttgggtg aacaaatggc tgacttgcac ttgtacaacc agaagttgag agaaaagttg    360
aaagaggaag agaacactgt tggtagaaga ggtgaaggtg ctgagccaca atacgttgac    420
aagttcggtt ccacactgt tacttgttgt ggtttcatcc cacaggttaa cgagtggcaa    480
gatgactggc caactttctt cgctagacac agattgcaag ctcagttgga cttgatcgag    540
aaggactacg ctgacagaga agctagaaa ttgtggtcca gattgcaggt taagatccca    600
gacttgttct gtggtttgga gatcgttcca gctttgttgc acggtgattt gtggtctggt    660
aacgttgctg aagatgacgt tggtccaatt atctacgacc cagcttcttt ctacggtcac    720
tctgaattcg agttggctat cgctttgatg ttcggtggtt tcccaagatc cttcttcact    780
gcttaccaca gaaagatccc aaaggctcca ggtttcgacc agagattgtt gttgtaccag    840
ttgttcaact acttgaacca ttggaaccac ttcggtagag agtacagatc tccatccttg    900
ggtactatga agaagattgt tgaagtaa                                        927
```

COMPOSITIONS FOR USE TO TREAT ADVANCED GLYCATION END PRODUCTS-DEPENDENT OCULAR DISEASES

CROSS-REFERENCE TO RELATED APPLICATIONS

This application is a national phase entry under 35 U.S.C. § 371 of International Patent Application PCT/EP2019/074058, filed Sep. 10, 2019, designating the United States of America and published as International Patent Publication WO 2020/053188 A1 on Mar. 19, 2020, which application claims the benefit under Article 8 of the Patent Cooperation Treaty to European Patent Application Serial No. 18194420.8, filed Sep. 14, 2018, and European Patent Application Serial No. 19184875.3, filed Jul. 8, 2019.

TECHNICAL FIELD

The disclosure relates to the treatment of vision impairment or blindness due to advanced glycation end products (AGEs)-related ocular diseases such as age-related presbyopia, macular degeneration (AMD), diabetic retinopathy (DR) and diabetic macular edema (DME) in a human or animal. Age-related presbyopia develops with anyone around the age of 40-50 years when elasticity of the ciliary body and the lens markedly decrease through accumulation of AGEs. Consequently, accommodation and the ability to read nearby decrease gradually. The only current solution for age-related presbyopia is a pair of reading glasses. AMD is the most common cause of irreversible loss of sight in persons>65 years in the western world. At this time, no treatment is available for the dry form of AMD. The dry form of AMD is characterized by vision threatening Drüsen, which are (sub)retinal accumulations of advanced glycation end products and fluorophores. DR and DME are—on the other hand—the most common cause of irreversible loss of sight in persons <65 years in the western world. Actual treatment options for DR and DME consist of topical and systemic steroids, anti-inflammatory agents, laser photocoagulation, pars plana vitrectomy and/or anti-Vascular Endothelial Growth Factor (VEGF) antibodies, but many patients show an inadequate response. DR and DME are characterized by the accumulation of AGEs in Bruch's membrane and in the retina due to hyperglycemia.

BACKGROUND

Presbyopia is an ageing condition everybody is confronted with from 40-50 years, decreasing near vision. The lens is held in position by a complex three-dimensional system of lens zonules, synthesized by the ciliary body. During accommodation, contraction of the ciliary body causes slackening of the lens zonules, resulting in increased curvature of the lens, and an increase in refractive power, owing to elasticity of the lens capsule and the outer cortical lens layers. With age, AGEs accumulate in the ciliary body, lens, and lens zonules closely associated with the collagenous material of the vitreous, and accommodative power decreases (1). Currently, the only treatment of age-related presbyopia consists in wearing a pair of reading glasses.

AMD is the leading cause of visual loss in the elderly in industrialized countries (2); 1 in 4 individuals aged over 75 years is affected by AMD. Late AMD can be broken down into two forms: the dry form (90%) and the wet or neovascular form (10%). Currently, treatment is only available for the neovascular form. This treatment consists of the intravitreal injection of anti-angiogenic agents with no evidence of any beneficial effect on the underlying degenerative process (3). Even under the best circumstances when eyes with wet AMD are treated and converted back to dry AMD, dry AMD will likely progress over time to vision loss. Dry AMD is associated with photoreceptor cell loss, often preceded by a compromise to the retinal pigment epithelium (RPE) cells.

Diabetes mellitus is predicted to affect about 300 million people by 2025. DR and DME are complications affecting about 25% of all patients with long-standing type 1 and type 2 diabetes mellitus. The United Kingdom Prospective Diabetes Study and the Diabetes Control and Complications Trial have confirmed the relationship between chronic hyperglycemia and the progression of DR and DME (1, 4). In diabetes, the retinal microvasculature becomes progressively dysfunctional in response to variable hyperglycemia. AGEs and/or late Amadori products have been localized to retinal vessels and neuroglia of diabetics. One of the key pathophysiological processes in DME, DR and AMD appears to be the formation of AGEs, leading to breakdown of the blood-retinal barrier, and upregulation of local inflammatory cytokines (prostaglandins, Il-6, TNF-α, PDGF-B), NFkB gene transcription and VEGF (5). Upregulation of VEGF causes angiogenesis with edema and bleedings in AMD, DR and DME. However, the actual treatment options focusing on treating complications and on VEGF as a molecular target do not target the root of the problem: the treatment of AGEs.

One function of RPE cells during the visual cycle is the regeneration of 11-cis retinal from all-trans retinal during the phototransduction cascade in the visual cycle. Another function of RPE cells is to phagocytose the tips of rods and cones saturated with dysfunctional retinaldehyde in bisretinoid fluorophores and AGEs, and to deposit this "lipofuscin" material at their basal lamina. Bisretinoids are generated as a byproduct of the visual cycle and mediate RPE cell senescence and expression of inflammatory chemokines that drive retina degeneration (6).

In the process of protein glycation, metabolically important sugars such as glucose and fructose react with primary amine groups (amino-terminus and ε-amino group of lysine), forming adducts that can then rearrange and react further, eventually leading to cross-links between proteins, which often inactivates these proteins or makes them resistant to the natural cellular degradation machinery. This process in which these AGEs are formed is also more generally known as the 'Maillard' reaction, which is in fact a very complex and, as yet, quite incompletely understood set of reactions. Maillard reactions have been shown to play a major role in the formation of lipofuscin in the retina (7).

During the process of photoreceptor disk renewal, the outer segment tips are shed in a diurnal manner and removed by the RPE cells in a short burst of phagocytic activity. Cone outer segments in the macula are similarly removed by the RPE cells, but the process is considerably slower. Phagocytosed outer segment tips are digested in the extensive RPE phagolysosomal system, a process that continues throughout life. Solubilized waste material is then transported across the basal infoldings of the RPE cells into the choriocapillaris. AGEs and bisretinoid complexes are thus formed at the level of the photoreceptors, then digested by the RPE cells, and finally accumulate in Drüsen and in the Bruch's membrane with age (8) and more specifically in AMD, DR and DME (9). AGEs can be detected in early disease as bright fluorescent dots in the retina, and with progression, AGE accumulations become larger and are encapsulated with calcium hydroxyapatite (10).

AGEs arise from two main sources: exogenous contributing around 30% of the total AGEs in the body, and endogenous contributing the remaining 70%. AGEs can thus be slowly formed from high concentration of blood sugar through the Maillard reaction or faster through reactions with alpha-dicarbonyls, such as methylglyoxal, glyoxal or 3-deoxyglucosane. The latter create a burden of AGEs in the lens and lens capsule, ciliary body, vitreous body, retina, cornea and optic nerve of the eye (1,5). The high oxygen concentration and environmental oxidative stress in vascularized parts of the eye, such as the retina and Bruch's membrane, contribute to the processes of oxidation that accelerate AGEs formation, making them especially vulnerable to the accumulation of AGEs. In DR, DME and AMD, excess deposition of these AGEs and bisretinoid complexes at the basal lamina damages the RPE and induces an inflammatory and degenerative reaction resulting in retinal atrophy, the expression of vascular endothelial growth factor (VEGF) and subsequent neovascularization, or both. The deposits are dynamic structures that can increase in size and fuse in most patients or regress very rarely (11). There are no early biomarkers to anticipate dry AMD and there are no therapies or cure. As the outer retina is glucose-rich, AGE formation is high in this tissue. Immunolocalization of AGEs such as pentosidine and carboxymethyllysine, and also RAGEs, has been shown in the retina already in early AMD and in DR and DME (5,12). Moreover, photodegradation of bisretinoid complexes generate dicarbonyls glyoxal and methylglyoxal, that are known to modify proteins by AGE formation (13)

The enzyme fructosamine-3-kinase has long been known to constitute part of the natural cellular repair capacity for the initial condensation product of glucose with protein primary amine groups (14). Its requirement for ATP as a co-substrate means that it requires a cellular context to work, and this has discouraged investigations with regard to potential therapeutic use. More importantly, the enzyme's action on advanced glycation end products (AGEs) and bisretinoids is unknown.

The vitreous body of the eye is a perfect reservoir for containing therapeutic agents in treating retinal diseases, as has already extensively been shown through the past 10 years. Anti-Vascular Endothelial Growth Factor antibodies (ranibizumab, bevacizumab), Vascular Endothelial Growth Factor decoy receptors (aflibercept), have been injected routinely into the vitreous for the treatment of hemorrhages in end stage AMD, diabetic retinopathy, DME, retinal vein occlusion, pathologic myopia since 2006 (15). The vitreous body is located between the eye lens and the retina and consists of an essentially acellular viscoelastic gel that contains more than 98% water, 2% hyaluronic acid, collagens type II and IX, fibronectin, fibrillin and opticin (16).

It is however completely unknown whether administering a deglycating enzyme such as fructosamine-3-kinase and its required cofactor(s) would result in the disruption of the Advanced Glycation End products and bisretinoid fluorophores. By deglycation of glycated byproducts of the visual cycle, the vicious circle of the formation of vision threatening Drüsen is broken down and a treatment for dry AMD, DR and DME is offered. It is completely unknown whether administering a deglycating enzyme as fructosamine-3-kinase and its required cofactor(s) to the ciliary body restores accommodation in age-related presbyopia.

The disclosure specifically relates to the administration of fructosamine-3-kinase and its cofactor(s) to a subject. This administration results in deglycation and inactivation of AGEs and fluorophores.

BRIEF DESCRIPTION OF THE DRAWINGS

FIG. 1 illustrates a system for intravitreal injecting deglycating enzymes according to an embodiment of the disclosure.

FIG. 2 histology of Drüsen in treated/untreated human retina. 5 micrometer sections of human retina with Drüsen (D) were treated with saline+ATP+MgCl$_2$ (FIG. 2A) or treated with F3K+ATP+MgCl$_2$ (FIG. 2B). The Drüse treated with saline+ATP+MgCl$_2$ (untreated Drüse) is encircled and is still intact and shows homogenous eosinophil material. The Drüse treated with F3K+ATP+MgCl$_2$ (treated Drüse) is encircled and is not intact anymore. The latter shows also less eosinophil material than the Drüse treated with saline+ATP+MgCl$_2$. Doses used ranged between about 4.17 and 12.5 µg/ml fructosamine-3-kinase, 2.50 and 4.17 mM ATP and 1.00 and 1.67 mM MgCl$_2$. (R=retina, C=choroid, S=sclera, D=encircled Drüse)

RGB intensity values were calculated of saline treated and FN3K treated Drüsen of human retinas (FIG. 2C). Mean intensity values were then calculated of 10 Drüsen treated with saline+ATP+MgCl$_2$ or with FN3K+ATP+MgCl$_2$ (FIG. 2D)

FIG. 3 NIR of Drüsen in treated/untreated human retina.

Figure 3A:
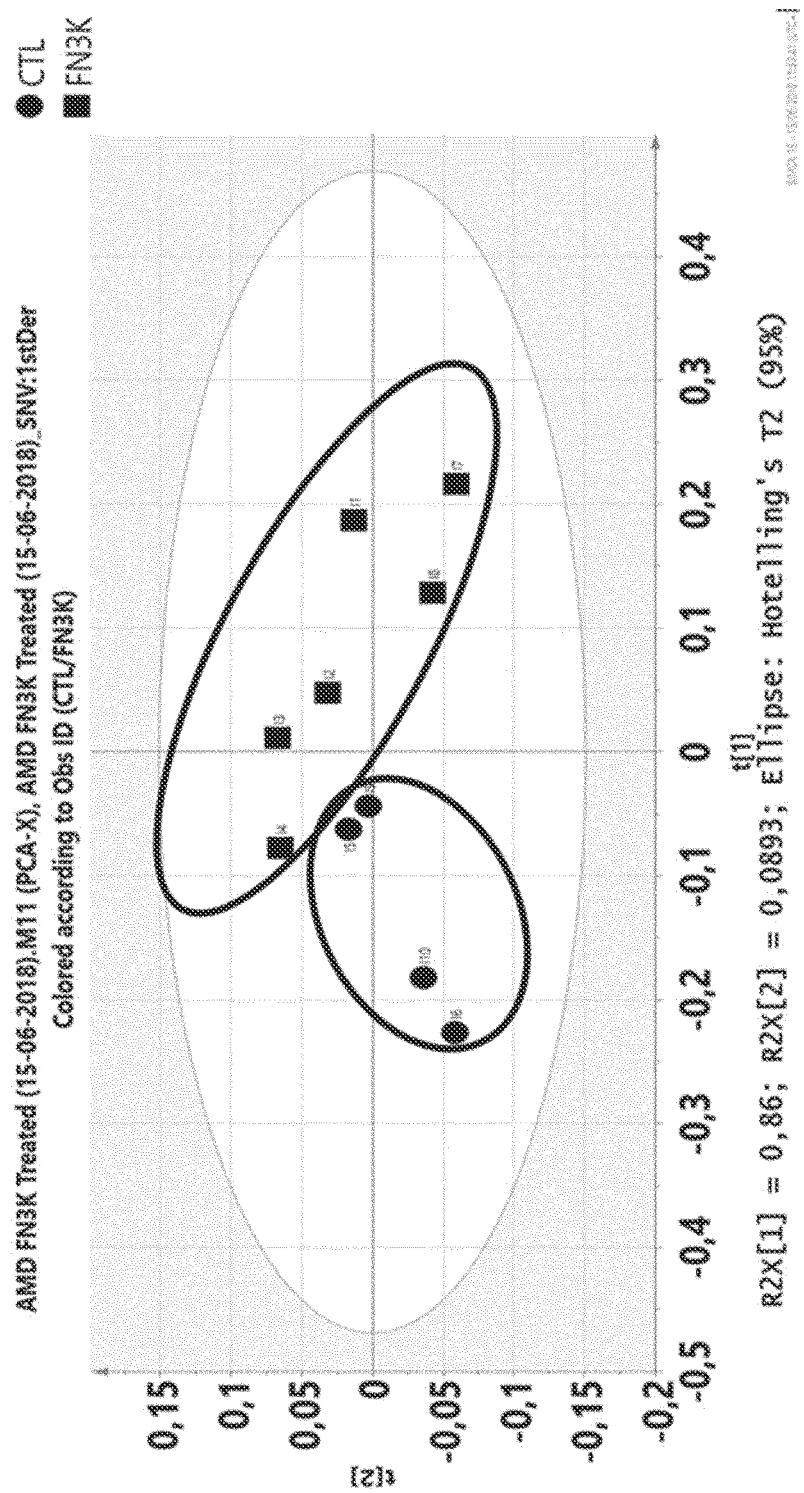

FIG. 3A: Hotelling's T2 plot of fluorescent AGEs in intraretinal Drüsen treated with saline+ATP+MgCl$_2$ (circles), compared to fluorescent AGEs in intraretinal Drüsen treated with F3K+ATP+MgCl$_2$ (squares) (FIG. 3A). Drüsen of 5 micron sections of human retina were treated for 6 hours with saline+ATP+MgCl$_2$ or with F3K+ATP+MgCl$_2$. Doses used ranged between about 4.17 and 12.5 µg/ml fructosamine-3-kinase, 2.50 and 4.17 mM ATP and 1.00 and 1.67 mM MgCl$_2$. Near infrared (NIR) spectra were recorded off-line using a NIR spectrometer equipped with an immobilized reflection probe of seven 400 µm fibers, an InGaAs detector and a halogen lamp (AvaSpecNIR256-2.5-HSC with an FCR-7UVIR400-2-BX reflection probe, Avantes). The Bruker Vertex 80v FTIR spectrometer was coupled to a Bruker Hyperion 2000 microscope for recording de FT-NIR transmission microspectra. The objective magnification of the microscope was set at 15× and the aperture at 20×20 µm. The background was collected with 800 co-adds. Spectra were recorded at a resolution of 16 cm$^{-1}$ in the range 12000-4000 cm$^{-1}$, and also collected with 800 co-adds. Spectral data analysis was performed using SIMCA software version 15.0 (MKS Data Analytics Solutions). Different preprocessing steps were performed to minimize irrelevant light scatter and standardize the spectroscopic signals. Differentiation was performed to accentuate small structural differences and reduce baseline effects[6], standard normal variate normalization was performed to eliminate multiplicative scaling effects and additive baseline offset variations[6,7] and finally a Savitzky-Golay based smoothing procedure was executed. After preprocessing, spectral data were analyzed by unsupervised pattern recognition methods, such as principal component analysis (PCA), and supervised pattern recognition methods such as partial least squares-discriminant analysis (PLS-DA).

As glycation results in a spectral shift in the near-infrared spectrum of proteins, it is possible to observe specific peak sharpening and spectral variations in NIR spectra due to deglycation of proteins.

FIG. 3B: Hotelling's T2 plot and spectral variations of fluorescent AGEs in Bruch's membrane treated with saline+ATP+MgCl$_2$ (control) or with FN3K+ATP+MgCl$_2$.

FIG. 3C: Hotelling's T2 plot and spectral variations of subretinal Drüsen treated with saline+ATP+MgCl$_2$ (control) or with FN3K+ATP+MgCl$_2$.

FIG. 3D: shows mean spectra of all measured NIR spectra of AGEs in Bruch's membrane (full lines) and of subretinal Drüsen (dotted lines) when treated with saline+ATP+MgCl2 (control) or treated with FN3K+ATP+MgCl2.

Results in FIG. 3 show that FN3K+ATP+MgCl2 treatment changes NIR spectra of AGEs at different histological levels: in retinal Drüsen (FIG. 3A), in Bruch's membrane (FIG. 3B) and in subretinal Drüsen (FIG. 3C)

FIG. 4: fluorometry of Drüsen in treated/untreated human retina: UV-fluorescence spectroscopy of Drüsen treated with saline+Mg+ATP (black line on top), compared to Drüsen treated with F3K+Mg+ATP (grey line below). Drüsen of 5 micron sections of human retina were treated for 6 hours with saline+ATP+MgCl$_2$ or with FN3K+ATP+MgCl$_2$. Fluorometry was performed with UV fluorescence spectroscopy in the range of 400 nm to 680 nm. Sharp differences were detected specifically in the range of AGE fluorescence (560 nm up to 680 nm).

Human neural retinas were isolated through dissection by a trained ophthalmologist from cadaver eyes that were rejected for corneatransplantation, within 12 h post-mortem and immediately transferred to a sterile 6-well plate. The retinas were carefully washed five times with 5 mL phosphate buffered saline (PBS) solution. Subsequently, maillard type fluorescence measurements (excitation 370 nm, emission 390-700 nm) were performed at baseline on each retina (30 different measurement locations) using a miniature spectrometer system (Flame-S-VIS-NIR, Ocean Optics, Largo, Fla.) at fixed distance and 90° angle. Afterwards, two milliliters of the final FN3K solution were added to each retina well, and human retinas were incubated for 24 h at 37° C. After the treatment procedure, all wells were washed five times with PBS and fluorescence measurements were performed again.

Figure 4A:
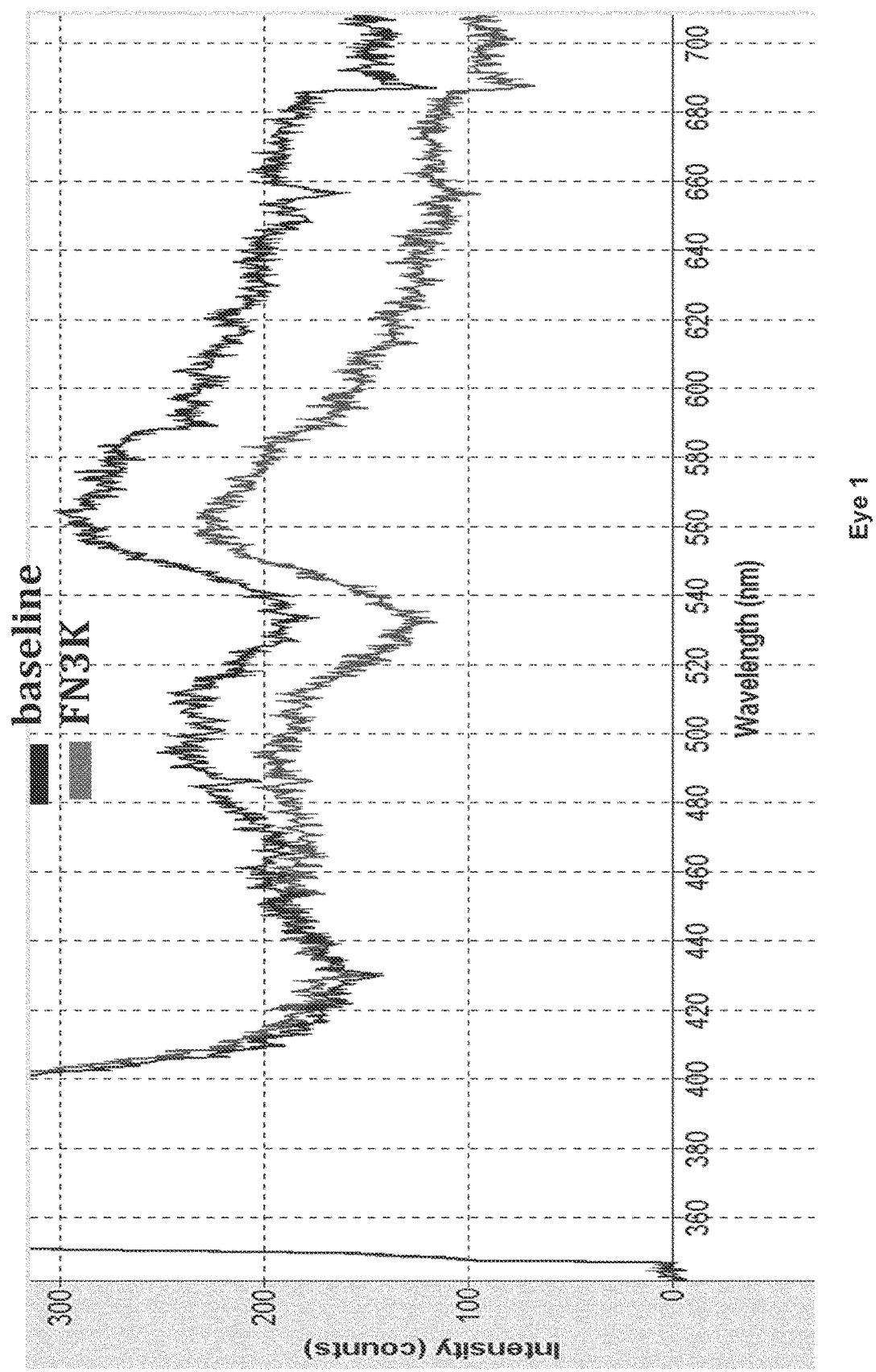

In total, intraretinal AGEs of five different human retinas of cadaver eyes were measured by UV-fluorescence spectroscopy in vitro. FIG. 4A shows fluorometry of intraretinal AGEs of eye of donor 1. FIG. 4B shows fluorometry of intraretinal AGEs in four other cadaver eyes (left eye of donor 2, left eye of donor 3, right eye of donor 3, left eye of donor 10).

Treatment with FN3K+ATP+MgCl$_2$ reduces fluorescence intensity of intraretinal AGEs.

FIG. 5 Tests are carried out on aged C57/Bl6 mice (>9 months old).

Mice were anesthetized with isoflurane 5% gas inhalation and sacrificed by neck luxation (according to declaration of Helsinki); both eyes were eviscerated and treated immediately by intravitreal injection. Of each mouse, one eye was treated with FN3K+ATP+MgCl$_2$ and the contralateral eye with saline+ATP+MgCl$_2$. Eyes were kept for 24 hours in 37° C. and then preserved in paraformaldehyde 2% for preparation for histological sections and staining with hematoxylin/eosin. Drüsen were present in eyes treated with saline, but no Drüsen were found in eyes treated with FN3K+ATP+MgCl$_2$. FIG. 5 shows round subretinal Drüse (thick arrow mouse 1) and thick flat subretinal Drüse in mouse 2 (thick arrow mouse 2) in the saline+ATP+MgCl$_2$ treated eyes, but no Drüsen were present in the FN3K+ATP+MgCl$_2$ treated eye of the same animal. Of note, the basal lamina (situated at triangle) in the saline+ATP+MgCl$_2$ treated eye of mouse 1 is completely disrupted but is complete over the whole line in the FN3K+ATP+MgCl$_2$ treated eye of the same mouse. No Drüsen are present and retinal pigment epithelial layers are intact in the FN3K+ATP+MgCl$_2$ treated eyes Histology in FIG. 5 shows that Drüsen are dissolved by Intravitreal injection with FN3K+ATP+MgCl$_2$ in an ex vivo mouse model.

Figure 6:
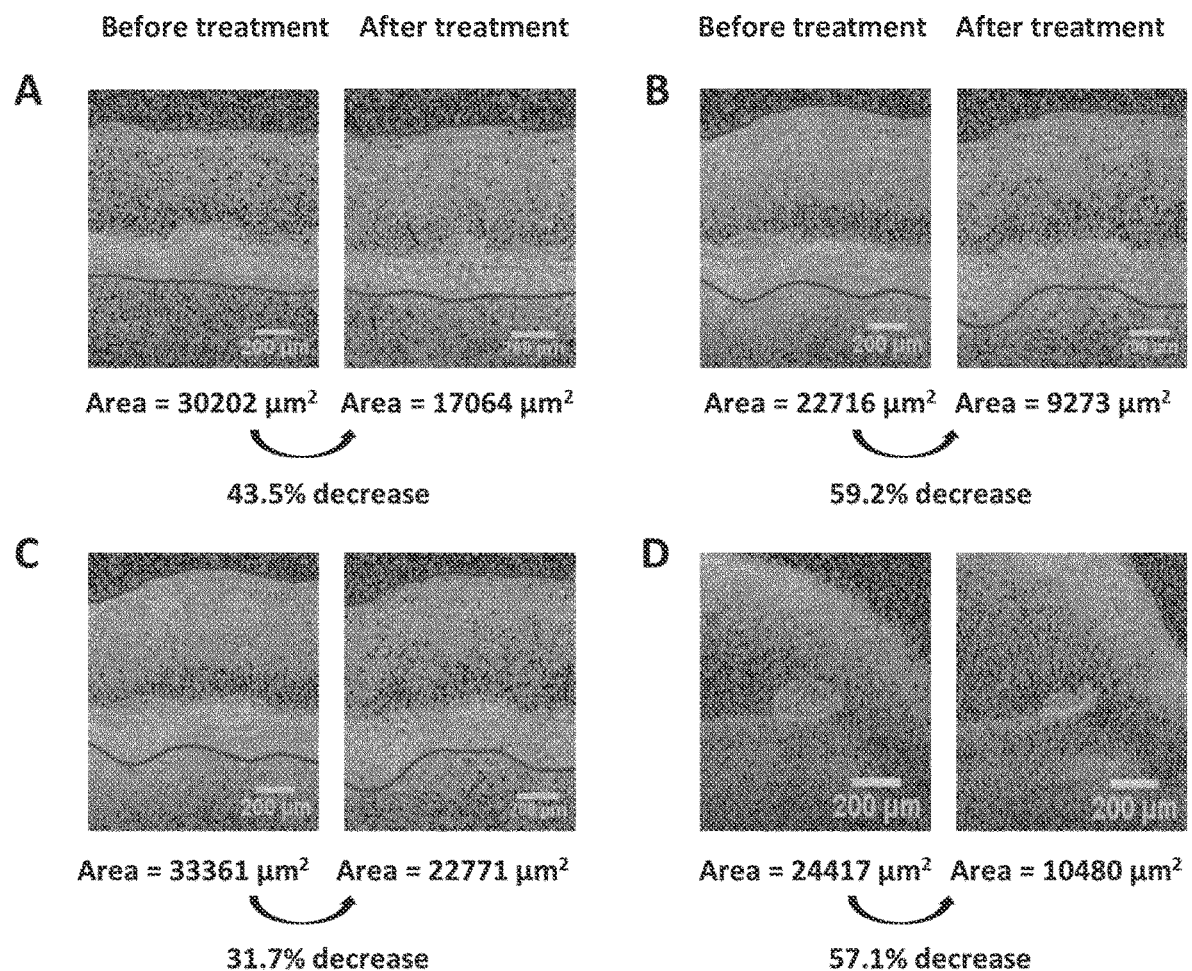

FIG. 6: Drüsen treated by intravitreal injection of FN3K+thiosulfate+hyaluronidase into a human cadaver eye.

Four human cadaver eyes (waste material rejected for corneal transplantation) were treated intravitreally with 50 μl FN3K+ATP+MgCl$_2$. Thiosulfate (0.1 mol/L) and hyaluronidase (5 U/ml) were added to the mixture to facilitate penetration of the hydroxyapatite crust around the Drüsen and the vitreous, respectively. Drüsen (encircled) were measured by spectroscopy (spectral domain Optical Coherence Tomography Van Hopplynus, Heidelberg, Germany) before injection and 3 hours after injection. The size of Drüsen is significantly reduced after FN3K treatment in a human ex vivo model.

Figure 7:
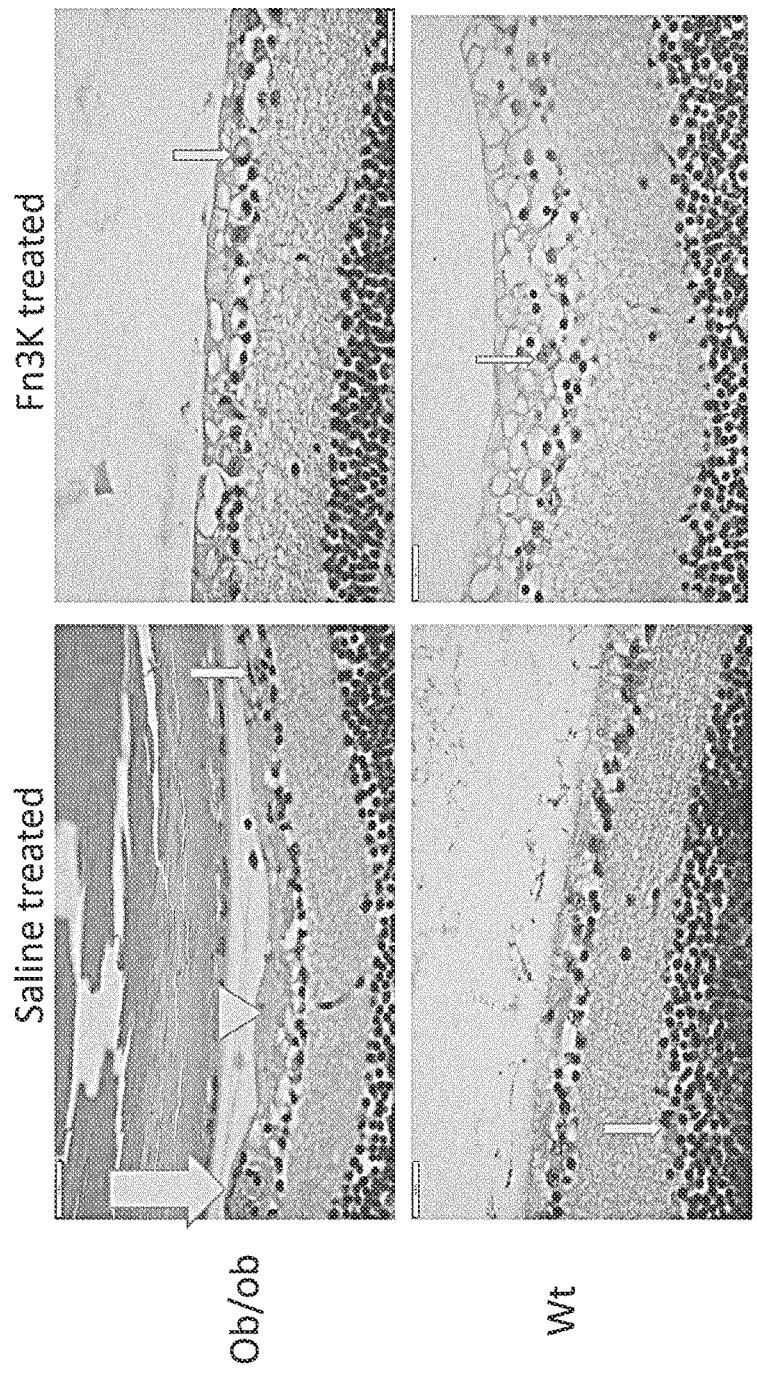

FIG. 7: FN3K treatment of retinas in ob/ob mice and wt mice by intravitreal injection in vivo.

Ob/ob mice of 26-30 weeks old were treated by intravitreal injection with 5 μl FN3K+ATP+MgCl$_2$ in one eye and with 5 μl saline+ATP+MgCl$_2$ in the other eye. Mice were sacrificed after 24 hours and eyes were collected and preserved in paraformaldehyde 2% for histology. Retinas of ob/ob mice treated with saline+ATP+MgCl$_2$ showed signs of diabetic retinopathy with large leaky vessels (large arrow), and a very thick collagenous inner limiting membrane (triangle). Retinas of ob/ob mice treated with FN3K+ATP+MgCl$_2$ showed normalization of the retina and normal microvasculature (small arrows) comparable with wt mice.

Figure 8:
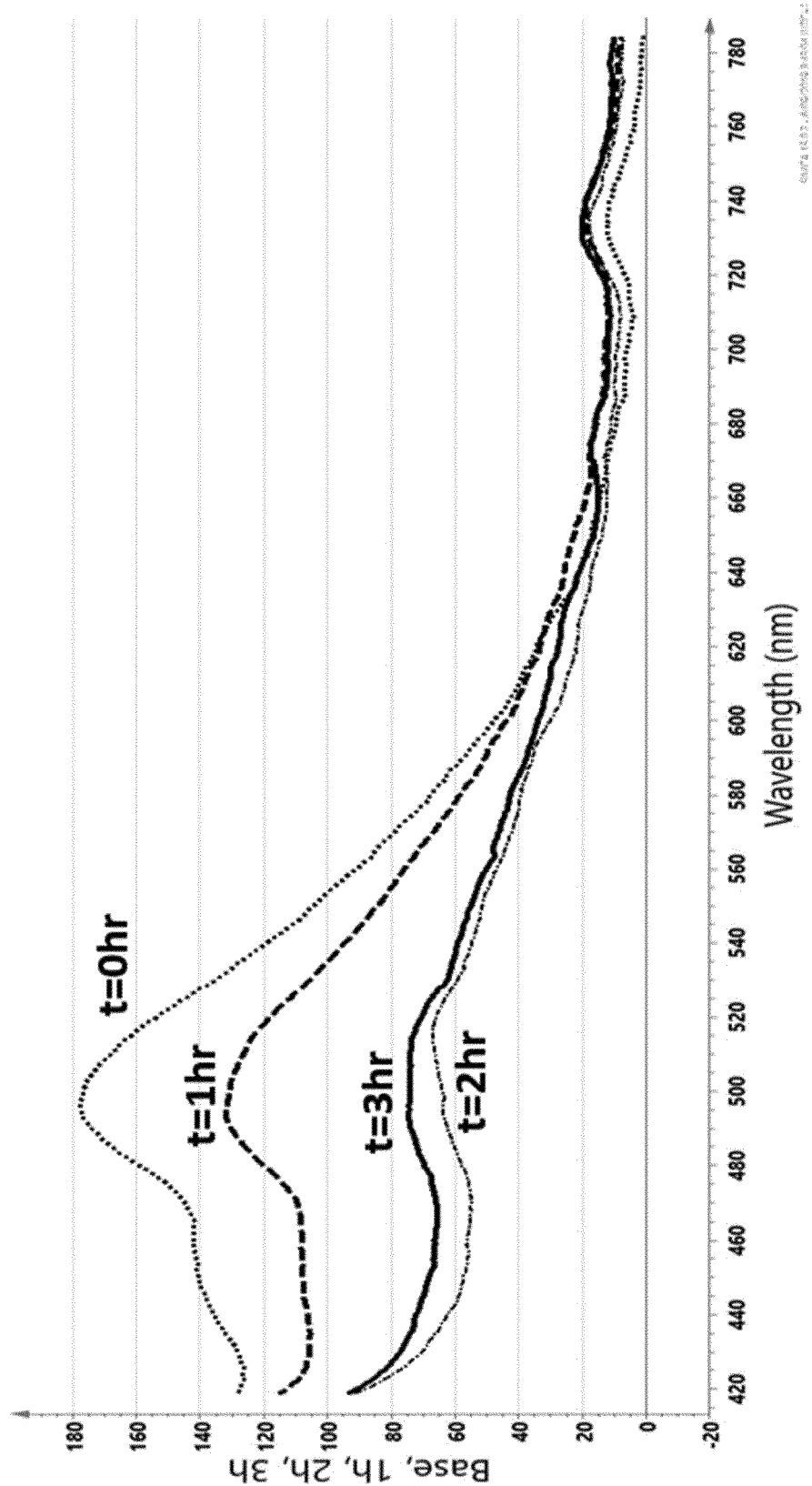

FIG. 8: FN3K treatment of AGEs in the ciliary body of human cadaver eyes in vitro.

Ciliary body was dissected from human cadaver eyes (waste material rejected for corneal transplantation) and treated for 3 hours ex vivo with 3 mL FN3K (41.6 μg/mL)+ATP 2.5 mmol/L+MgCl2 (1 mmol/L). Baseline Fluorometry was performed (0 hr dotted line) and after FN3K treatment for 1 hour (dashed line), 2 hours (full line) and 3 hours (line with stripes and dots) using a miniature spectrometer system (Flame-S-VIS-NIR, Ocean Optics, Largo, Fla.) at fixed distance and 90° angle. QR400-7-VIS-BX Premium 400 micron reflection probe was used. Treatment of the ciliary body with FN3K reduces fluorescent signal of AGEs at 490 nm wavelength.

FIG. 9: FN3K treatment of human cadaver eyes by external application of FN3K drops ex vivo.

Human cadaver eyes (waste material rejected for corneal transplantation) were treated within 24 hours after prelevation. For cross over experiments, always two eyes from the same donor are used.

Figure 9A:
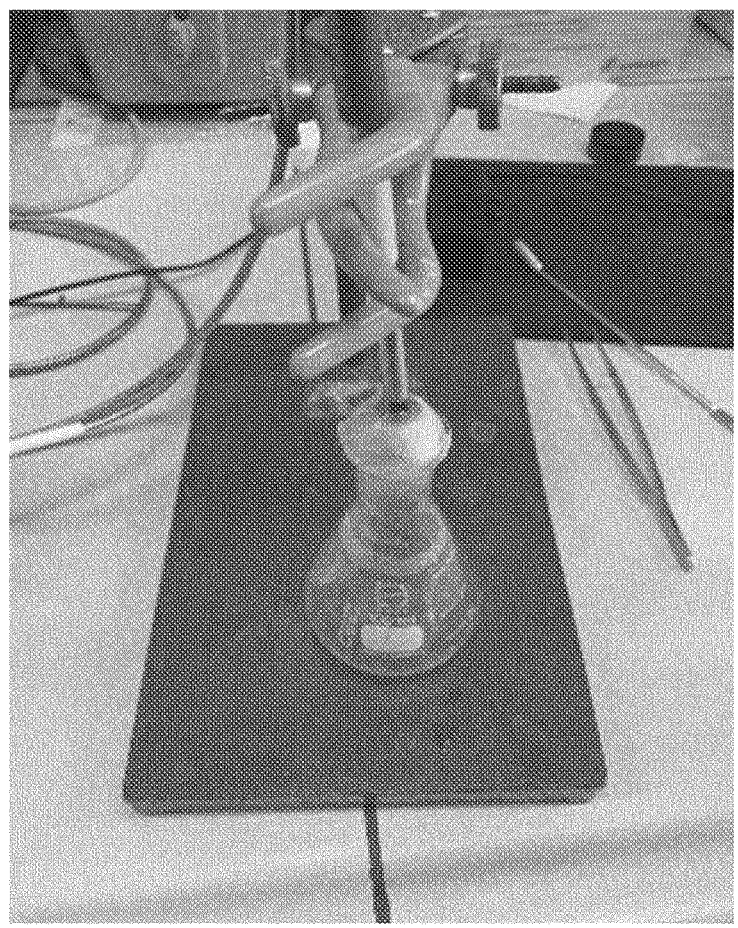

FIG. 9A shows technique of applying FN3K drops to the intact human cadaver eye. 6 to 7 drops of FN3K (25 μg/mL)+ATP (5 mmol/L)+MgCl2 (2 mmol/L) solution were applied every hour for 6 hours on one eye and saline drops were applied every hour for 6 hours on the other eye from the same donor. Fluorometry was performed at baseline before treatment and after treatment using a miniature spectrometer system (Flame-S-VIS-NIR, Ocean Optics, Largo, Fla.) at fixed distance and 90° angle. QR400-7-VIS-BX Premium 400 micron reflection probe was used.

FIG. 9B: Fluorescent signal of AGEs is lower in eye 1 than in eye 2 at the start of the experiment (t=0 hr) Eye 1 is then treated with FN3K drops for 6 hours while eye 2 is treated with saline drops. Fluorescent signal of AGEs measured after 6 hours of treatment (t=6 hr) however only drops in the FN3K treated eye. When pursuing the experiment as a cross-over experiment, eye 1 is then treated with saline drops for another 6 hours and eye 2 with FN3K drops. Fluorescent signal of AGEs is measured again (t=12 hr). Fluorescent signal of AGEs decreases significantly in eye 2 but not in eye 1.

FIG. 9 shows that FN3K treatment of the intact human eye by external application such as FN3K drops reduces fluorescent signal of AGEs in the eye.

DETAILED DESCRIPTION

The disclosure relates to the surprising finding that the administration of a fructosamine-3-kinase and its co-factor(s) results in less/less dense Drüsen in AMD. In other words, the latter administration restores light transmission and thus vision in patients with AMD.

The disclosure also relates to the surprising finding that treatment with fructosamine-3-kinase and its co-factor(s) reduces AGEs in the retina, in Bruch's membrane, and subretinal. In other words, a composition comprising FN3K and adenosine tri phosphate restores light transmission and thus vision in patients with AGE-dependent ocular diseases such as AMD, DR and DME.

The disclosure also relates to the finding that treatment with fructosamine-3-kinase and its cofactor(s) reduces AGEs in the ciliary body. In other words, a composition comprising FN3K and its cofactors restores accommodation and thus near vision in individuals with age-related presbyopia.

The disclosure thus in first instance relates to a composition comprising a fructosamine-3-kinase and adenosine tri phosphate for use to treat AMD, DR and/or DME, age-related presbyopia in a human or an animal.

The disclosure further relates a composition for use as described above wherein the composition is administered by intravitreal injection.

The disclosure further relates to a composition for use as described above which further comprises magnesium ions and/or an adenosine tri phosphate regenerating system.

The disclosure further relates to a composition comprising a fructosamine-3-kinase and adenosine tri phosphate regenerating system for use to treat AMD, DR and/or DME in a human or an animal wherein the composition is administered by intravitreal injection.

The disclosure further relates a composition comprising a fructosamine-3-kinase and adenosine tri phosphate regenerating system for use as described above which further comprises magnesium ions.

The term 'a fructosamine-3-kinase' relates to enzymes classified as enzymes 2.7.1.171 in, for example, the Brenda enzyme database. The latter enzymes are part of an ATP-dependent system for removing carbohydrates from non-enzymatically glycated proteins and catalyze the following reaction: ATP+ [protein]-N6-D-fructosyl-L-lysine=ADP+ [protein]-N6-(3-O-phospho-D-fructosyl)-L-lysine. More specifically, the term 'a fructosamine-3-kinase' relates to— as a non-limiting example—to the human fructosamine-3-kinase having accession number or the National Center for Biotechnology Information (NCBI) Reference sequence number: NP 071441.1. It should be further clear that the term 'a fructosamine-kinase' relates to the enzymes as described above, but also to functional fragments and variants thereof. The term "functional fragments and variants" relates to fragments and variants of the naturally occurring enzymes. Indeed, for many applications of enzymes, part of the protein may be sufficient to achieve an enzymatic effect. The same applies for variants (i.e., proteins in which one or more amino acids have been substituted with other amino acids, but which retain functionality or even show improved functionality), in particular, for variants of the enzymes optimized for enzymatic activity (as is also described further with regard to recombinant enzymes). The term 'fragment' thus refers to an enzyme containing fewer amino acids than the 309 amino acid sequence of the human fructosamine-3-kinase having NCBI Reference sequence number: NP_071441.1 and that retains the enzyme activity. Such fragments can, for example, be a protein with a deletion of 10% or less of the total number of amino acids at the C- and/or N-terminus. The term "variant" thus refers to a protein having at least 50% sequence identity, preferably having at least 51-70% sequence identity, more preferably having at least 71-90% sequence identity or most preferably having at least 91, 92, 93, 94, 95, 96, 97, 98 or 99% sequence identity with the 309 amino acid sequence of the human fructosamine-3-kinase having NCBI Reference sequence number: NP_071441.1 and that retains the enzyme activity.

Hence, orthologues, or genes in other genera and species (than the human fructosamine-3-kinase having NCBI Reference sequence number: NP_071441.1) with at least 50% identity at amino acid level, and having the enzyme activity are part of the disclosure. The percentage of amino acid sequence identity is determined by alignment of the two sequences and identification of the number of positions with identical amino acids divided by the number of amino acids in the shorter of the sequences×100. The latter 'variant' may also differ from the protein having NCBI Reference sequence number: NP_071441.1 only in conservative substitutions and/or modifications, such that the ability of the protein to have enzymatic activity is retained. A "conservative substitution" is one in which an amino acid is substituted for another amino acid that has similar properties, such that one skilled in the art of protein chemistry would expect the nature of the protein to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. (13,14)

Variants may also (or alternatively) be proteins as described herein modified by, for example, the deletion or addition of amino acids that have minimal influence on the enzymes activity as defined above, secondary structure and hydropathic nature of the enzyme.

The terms 'adenosine tri phosphate' (ATP) and 'magnesium ions' relate to well-known cofactors of the latter enzymes.

The term 'adenosine tri phosphate generating system' relates to several enzymatic and whole-cell based methods to regenerate ATP from ADP or AMP as are, for example, described by Woodyer R. D. et al. 2006 (15,16). In particular, the latter term refers to the following four enzymes commonly used in the regeneration of ATP from ADP: 1) the use of phosphoenolpyruvate in a coupled reaction catalyzed by pyruvate kinase, 2) acetylphosphate coupled with acetate kinase, 3) creatine phosphate coupled with creatine kinase, and 4) polyphosphate coupled with polyphosphate kinase. Preferably, the term 'ATP generating system' refers to the usage of phosphocreatine as a secondary energy source and creatine kinase to transfer its phosphate group to ADP to regenerate ATP. The usage of the latter ATP generating systems thus limits the concentration of ATP present in the mixture injected into the vitreous body as is also described further.

The terms 'to treat AMD and/or DR and/or DME' relate to stabilization and/or improving vision of the treated subject.

The term "to treat age-related presbyopia" relates to stabilization and/or improving nearby vision of the treated subject.

The term 'animal' may relate to any animal.

The terms 'administration by intravitreal injection' relate to injection of the compounds of the disclosure into the vitreous body of the eye. The intravitreal injection technique is used under controlled aseptic conditions. Adequate anesthesia is given prior to the injection. For the treatment of animal eyes, general anesthesia is used by, for example, inhalation anesthesia with isoflurane 5%. For the treatment of humans, local anesthetic drops can be used. A 32-gauge needle can be used for injection in smaller animal (such as a small rodent) eyes and a 30-gauge needle in human eyes and eyes of bigger animals such as horse and pig. In all species, the sclera is penetrated at an angle from 45°-90°. In mouse, for example, the sclera can be penetrated at 1-1.5 millimeter from the limbus; and in humans, the sclera can be penetrated at 3-5 millimeter from the limbus. The needle passes through the sclera and choroid until the vitreous body is reached. The needle does not touch the lens, nor the retina. The composition of the disclosure can be as such delivered and the needle is withdrawn immediately.

The disclosure thus relates—in other words—to a method to treat (or prevent) age-related presbyopia, AMD, DR and/or DME in a subject in need thereof wherein the method comprises administering (for example, by an injection of) a therapeutically effective amount of a compound comprising a fructosamine-3-kinase and adenosine tri phosphate, or, a fructosamine-3-kinase and an adenosine tri phosphate generating system, or, a fructosamine-3-kinase and adenosine tri phosphate and an adenosine tri phosphate generating system, or a fructosamine-3-kinase and adenosine tri phosphate and magnesium ions, or, a fructosamine-3-kinase and adenosine tri phosphate and an adenosine tri phosphate generating system and magnesium ions, or, a fructosamine-3-kinase and an adenosine tri phosphate generating system and magnesium ions to (for example, in the vitreous body of) the eye of the subject.

The term 'a therapeutically effective amount' relates to an amount ranging from 5 µl (for administering/injecting into a single mouse eye) to 50 µl (for administering/injecting into a single bovine eye) taken from a therapeutic dose ranging between about 4.17 and 12.5 µg/ml fructosamine-3-kinase, 2.50 and 4.17 mM ATP and 1.00 and 1.67 mM MgCl2. The latter therapeutic doses can be obtained by mixing 1:1, 1:2, 1:3 or 1:5 a solution of 25 µg/ml fructosamine-3-kinase with a fresh solution of 5 mM ATP/2 mM MgCl$_2$.

0.1 mol/L thiosulfate and 5 U/ml hyaluronidase are added to the mixture when amounts >5 µl are administered (intravitreally) in an animal eye (not mouse) and human eyes.

It should be clear that besides 'injecting' the therapeutically effective amounts 'intravitreally,' which is one way of administration, also other means of administration are envisioned such as, but not limited to, external application such as via drops or gels, and, other internal applications such as suprachoroidal injections or subretinal injections or implants everywhere else in the eye. Hence, and for example, the disclosure therefore relates to a composition comprising a fructosamine-3-kinase and ATP (and which might further comprise magnesium ions) for use to treat age-related presbyopia wherein the composition is administered by intravitreal injection or as external application.

The disclosure further relates to a composition as indicated above wherein the fructosamine-3-kinase is a recombinant fructosamine-3-kinase. The term 'recombinant' refers to fructosamine-3-kinase obtained as an outcome of the expression of recombinant DNA encoding for a fructosamine-3-kinase inside living cells such as bacteria or yeast cells. Practitioners are further directed to Sambrook et al. Molecular Cloning: A laboratory Manual, 4$^{th}$ ed., Cold Spring Harbor press, Plainsview, New York (2012) and Ausubel et al. Current Protocols in Molecular Biology (supplement 114), John Wiley & Sons, New York (2016).

More specifically the disclosure relates to a recombinant fructosamine-3-kinase, which is obtainable by recombinant production in *Pichia pastoris* and, even more specifically, wherein the recombinant fructosamine-3-kinase obtainable by recombinant production in *Pichia pastoris* has the amino acid sequence as given by SEQ ID NO:1 or SEQ ID NO:2. SEQ ID NO:1 is a construct with an N-terminal cleavable HIS-tag and a caspase 3-cleavable Asp-Glu-Val-Asp (DEVD) linker between the His6 tag and the protein coding sequence, which allows for clean removal of the tag. SEQ ID NO:2 is the cleaved version of SEQ ID NO:1.

The amino acid sequences of SEQ ID NO:1 and SEQ ID NO:2 (and their encoding nucleic acid sequences SEQ ID NO:3 and SEQ ID NO:4, respective) are as follows:

```
SEQ ID NO: 1:
Type: amino acid 1-letter (underlined: His6-tag, italics: linker,
bold underlined: caspase cleavage site)
MHHHHHH*VNGPGS*__DEVD__EQLLRAELRTATLRAFGGPGAGCISEGRAYD

TDAGPVFVKVNRRTQARQMFEGEVASLEALRSTGLVRVPRPMKVIDLPGGGAAFVMEH

LKMKSLSSQASKLGEQMADLHLYNQKLREKLKEEENTVGRRGEGAEPQYVDKFGFHT

VTCCGFIPQVNEWQDDWPTFFARHRLQAQLDLIEKDYADREARELWSRLQVKIPDLFCG

LEIVPALLHGDLWSGNVAEDDVGPIIYDPASFYGHSEFELAIALMFGGFPRSFFTAYHRKI

PKAPGFDQRLLLYQLFNYLNHWNHFGREYRSPSLGTMRRLLK*

SEQ ID NO: 3:
Type: DNA (underlined: His6-tag, italics: linker, bold underlined:
caspase cleavage site)
ATGCATCATCATCATCATCAT*GTTAACGGTCCAGGTTCT*__GATGAAGTT__

__GAT__GAACAGTTGTTGAGAGCTGAGTTGAGAACTGCTACTTTGAGAGCTTTTGGTGGT

CCAGGTGCTGGTTGTATTTCTGAGGGTAGAGCTTACGATACTGACGCTGGTCCAGTT
```

-continued

```
TTCGTTAAGGTTAACAGAAGAACTCAGGCTAGACAGATGTTCGAGGGTGAAGTTGC

TTCTTTGGAGGCTTTGAGATCCACTGGTTTGGTTAGAGTTCCAAGACCAATGAAGGT

TATCGACTTGCCAGGTGGTGGTGCTGCTTTTGTTATGGAACACTTGAAGATGAAGTC

CTTGTCCTCCCAGGCTTCTAAGTTGGGTGAACAAATGGCTGACTTGCACTTGTACAA

CCAGAAGTTGAGAGAAAAGTTGAAAGAGGAAGAGAACACTGTTGGTAGAAGAGGT

GAAGGTGCTGAGCCACAATACGTTGACAAGTTCGGTTTCCACACTGTTACTTGTTGT

GGTTTCATCCCACAGGTTAACGAGTGGCAAGATGACTGGCCAACTTTCTTCGCTAGA

CACAGATTGCAAGCTCAGTTGGACTTGATCGAGAAGGACTACGCTGACAGAGAAGC

TAGAGAATTGTGGTCCAGATTGCAGGTTAAGATCCCAGACTTGTTCTGTGGTTTGGA

GATCGTTCCAGCTTTGTTGCACGGTGATTTGTGGTCTGGTAACGTTGCTGAAGATGA

CGTTGGTCCAATTATCTACGACCCAGCTTCTTTCTACGGTCACTCTGAATTCGAGTTG

GCTATCGCTTTGATGTTCGGTGGTTTCCCAAGATCCTTCTTCACTGCTTACCACAGAA

AGATCCCAAAGGCTCCAGGTTTCGACCAGAGATTGTTGTTGTACCAGTTGTTCAACT

ACTTGAACCATTGGAACCACTTCGGTAGAGAGTACAGATCTCCATCCTTGGGTACTA

TGAGAAGATTGTTGAAGTAA
```

SEQ ID NO: 2 (= FN3K after N-terminal HIS-tag removal):
Type: amino acid 1-letter

```
EQLLRAELRTATLRAFGGPGAGCISEGRAYDTDAGPVFVKVNRRTQAR

QMFEGEVASLEALRSTGLVRVPRPMKVIDLPGGGAAFVMEHLKMKSLSSQASKLGEQM

ADLHLYNQKLREKLKEEENTVGRRGEGAEPQYVDKFGFHTVTCCGFIPQVNEWQDDW

PTFFARHRLQAQLDLIEKDYADREARELWSRLQVKIPDLFCGLEIVPALLHGDLWSGNV

AEDDVGPIIYDPASFYGHSEFELAIALMFGGFPRSFFTAYHRKIPKAPGFDQRLLLYQLFN

YLNHWNHFGREYRSPSLGTMRRLLK*
```

SEQ ID NO: 4:
Type: DNA

```
GAACAGTTGTTGAGAGCTGAGTTGAGAACTGCTACTTTGAGAGCTTT

TGGTGGTCCAGGTGCTGGTTGTATTTCTGAGGGTAGAGCTTACGATACTGACGCTGG

TCCAGTTTTCGTTAAGGTTAACAGAAGAACTCAGGCTAGACAGATGTTCGAGGGTGA

AGTTGCTTCTTTGGAGGCTTTGAGATCCACTGGTTTGGTTAGAGTTCCAAGACCAAT

GAAGGTTATCGACTTGCCAGGTGGTGGTGCTGCTTTTGTTATGGAACACTTGAAGAT

GAAGTCCTTGTCCTCCCAGGCTTCTAAGTTGGGTGAACAAATGGCTGACTTGCACTT

GTACAACCAGAAGTTGAGAGAAAAGTTGAAAGAGGAAGAGAACACTGTTGGTAGA

AGAGGTGAAGGTGCTGAGCCACAATACGTTGACAAGTTCGGTTTCCACACTGTTACT

TGTTGTGGTTTCATCCCACAGGTTAACGAGTGGCAAGATGACTGGCCAACTTTCTTC

GCTAGACACAGATTGCAAGCTCAGTTGGACTTGATCGAGAAGGACTACGCTGACAG

AGAAGCTAGAGAATTGTGGTCCAGATTGCAGGTTAAGATCCCAGACTTGTTCTGTGG

TTTGGAGATCGTTCCAGCTTTGTTGCACGGTGATTTGTGGTCTGGTAACGTTGCTGAA

GATGACGTTGGTCCAATTATCTACGACCCAGCTTCTTTCTACGGTCACTCTGAATTCG

AGTTGGCTATCGCTTTGATGTTCGGTGGTTTCCCAAGATCCTTCTTCACTGCTTACCA

CAGAAAGATCCCAAAGGCTCCAGGTTTCGACCAGAGATTGTTGTTGTACCAGTTGTT

CAACTACTTGAACCATTGGAACCACTTCGGTAGAGAGTACAGATCTCCATCCTTGGG

TACTATGAGAAGATTGTTGAAGTAA
```

The disclosure indeed relates—in addition—to the finding that the recombinant fructosamine-3-kinase obtainable by recombinant production in Pichia pastoris and having the amino acid sequence as given by SEQ ID NO:1 and 2 are preferred enzymes for treating AMD. Indeed, the latter enzymes are preferred as 1) their production in Pichia resulted in higher yields of the enzyme compared with the production in, for example, E. coli, 2) the enzymes had a higher purity when analyzed on SDS page, and 3) the presence of endotoxin, which is known to provoke an ocular inflammation during intravitreal injection, can be avoided.

The following examples are provided to better illustrate the disclosure and should not be considered as limiting the scope of the disclosure.

EXAMPLES

Example 1: Recombinant Production of Fructosamine-3-Kinase

A gene coding for human fructosamine-3-kinase (having accession number or the National Center for Biotechnology Information (NCBI) Reference sequence number: NP_071441.1, codon-optimized for Pichia pastoris expression (SEQ ID NO:1), was cloned into the pKai61 P. pastoris expression vector according to Claes, K. et al. ("Modular Integrated Secretory System Engineering in Pichia Pastoris To Enhance G-Protein Coupled Receptor Expression," ACS Synthetic Biology 5, no. 10 (Oct. 21, 2016): 1070-75). The encoded gene contains an N-terminal His6-tag (MHHHHHH) in frame with a caspase-3 cleavage site (DEVD) and the expression is under control of the methanol inducible AOX1 promoter. The plasmid contains a zeocin resistance marker for selection in bacterial as well as in yeast cells. The vectors were linearized in the AOX1 promoter before transformation to P. pastoris (strain NRRL Y-11430) to promote homologous recombination in the endogenous AOX1 locus for stable integration into the genome.

Stable integrants were grown shaking at 28° C. in BMY buffered complex medium (10 g/L yeast extract, 20 g/L peptone, 100 mM potassium phosphate buffer pH 6.0, 13.4 g/L YNB without amino acids) complemented with 1% glycerol. After 48 hours of growth, recombinant expression was induced by transfer to BMY medium complemented with 1% methanol. After 48 hours of expression, cultures were centrifuged, supernatant was discarded and pellets were flash frozen in liquid nitrogen and stored at −20° C.

Pellets were thawed and resuspended in washing buffer for protein extraction. Pichia pastoris cells were mechanically disrupted using 0.5 mm glass or silica/zirconium beads. The cleared supernatant was purified by $Ni^{2+}$ affinity chromatography for the His6-tagged fructosamine-3-kinase, followed by gel filtration. The protein eluted in FN3K sample buffer (20 mM Tris-HCl pH 8.0, 150 mM NaCl, 1 mM DTT) was identified as recombinant human fructosamine-3-kinase by SDS-PAGE and Western blotting with antibodies against the His6-tag and human FN3K (ThermoFisher). Enzymatic activity was confirmed in a kinase activity assay with a 1 deoxy 1 morpholino D fructose substrate (R&D Systems). Fructosamine-3-kinase aliquots were flash frozen in liquid nitrogen and stored at −20° C.

Example 2: Treatment of 5 Micron Slices of Human Eyes with Drüsen 5 micrometer sections of human retina with Drüsen (D) are treated with saline+ATP+$MgCl_2$ or treated with FN3K+ ATP+$MgCl_2$. Doses used ranged between about 4.17 and 12.5 μg/ml fructosamine-3-kinase, 2.50 and 4.17 mM ATP and 1.00 and 1.67 mM $MgCl_2$. Drüsen are evaluated by light microscopy for integrity and presence of eosinophil material (FIGS. 2A and B).

Stained tissue sections were scanned by the Olympus dotSlide Digital Virtual Microscopy System and processed using the OlyVIA viewer program (Olympus Corporation, Tokyo, Japan). For subsequent image analysis, the freeware ImageJ v1.8.0 downloaded from the NIH website was used. Red (R), green (G) and blue (B) intensity values were calculated using the RGB Measure plug-in. FIG. 2C shows intensity values on the RGB color histogram of the histological section of a Drüse when treated with saline+ATP+$MgCl_2$ (untreated) or treated with FN3K+ATP+$MgCl_2$. FIG. 2D shows mean value of all intensity values of 10 Drüsen treated with saline+ATP+$MgCl_2$ (untreated) and 10 FN3K treated Drüsen with Near infrared (NIR) spectra are recorded off-line using a NIR spectrometer equipped with an immobilized reflection probe of seven 400 μm fibers, an InGaAs detector and a halogen lamp (AvaSpecNIR256-2.5-HSC with an FCR-7UVIR400-2-BX reflection probe, Avantes). As glycation results in a spectral shift in the near-infrared spectrum of proteins, it is possible to observe specific peak sharpening and spectral variations in NIR spectra due to deglycation of proteins (FIG. 3). FIG. 3A shows the Hotelling's T2 plot of intraretinal AGEs in human retina treated with saline+Mg $Cl_2$+ATP (circles), compared to intraretinal AGEs in human retina treated with FN3K+Mg $Cl_2$+ATP (squares).

FIG. 3B shows NIR spectra and Hotelling's plot of AGEs in Bruch's membrane treated with saline+Mg $Cl_2$+ATP (control) compared to AGEs in Bruch's membrane treated with FN3K+Mg $Cl_2$+ATP. FIG. 3C shows NIR spectra and Hotelling's plot of AGEs in subretinal Drüsen treated with saline+Mg $Cl_2$+ATP (control) compared to AGEs in subretinal Drüsen treated with FN3K+Mg $Cl_2$+ATP.

FIG. 3D shows mean spectra of measured NIR spectra of AGEs in Bruch's membrane (full lines) and in subretinal Drüsen (dotted lines) when treated with saline+ATP+$MgCl_2$ (control) or treated with FN3K+ATP+$MgCl_2$ Fluorometry of Drüsen is performed on 5 micron sections of human retina treated with saline+ATP+$MgCl_2$ (circles) or with FN3K+ATP+$MgCl_2$ (squares). Fluorometry is performed with UV fluorescence spectroscopy in the range of 400 nm to 680 nm. Differences are detected specifically in the range of AGE fluorescence (560 nm up to 680 nm) (FIG. 4). Fluorometry is performed on five different retinas of human cadaver eyes. FIG. 4 shows measurements of AGEs of intraretinal Drüsen. FIG. 4A shows raw AGE fluorescence spectroscopy curves of eye 1. FIG. 4B shows AGE fluorescence spectroscopy results of four other human retinas after smoothening of the curves.

Mean fluorescence intensities of the four latter human retinas are then calculated and compared (Table 1).

TABLE 1

Mean fluorescence intensity 420-700 nm (a.u.) of human neural retinas at baseline and after ex vivo FN3K treatment

|  | Baseline | FN3K | % change | P-value |
|---|---|---|---|---|
| Eye 2 left Eye 3 | 63.2 (55.9) | 43.7 (42.4-51.3) | −31.2 | <0.0001 |
| left | 55.5 (52.4-60.5) | 42.5 (41.0-44.0) | −23.4 | <0.0001 |
| right | 75.3 (68.2-78.9) | 50.7 (45.9-56.5) | −32.7 | <0.0001 |
| Eye 10 left | 71.5 (50.1-95.9) | 56.1 (50.4-76.7) | −21.5 | 0.14 |

Example 3: Treatment of Eyes of Aged C57/Bl6 Mice. In Vivo Experiment

Tests are carried out on aged C57/Bl6 mice, which show the typical AMD lesions as Drüsen. Following FN3K treatment in one eye by intravitreal injection, mice retinas are studied using near-infrared (NIR) and fluorescence spectroscopy.

Histological sections are performed to evaluate the presence or absence of the typical Drüsen (FIG. 5) Drüsen were present when the eyes were treated with intravitreal injection of saline+ATP+MgCl$_2$ but were absent when eyes (contralateral eye of the same animal) were treated with FN3K+ATP+MgCl$_2$ Mice from 23 months old are anesthetized during the surgical procedure with inhalation anesthesia (isoflurane 5%). Both eyes of the same animal are injected, one with 5 microliter fructosamine-3 kinase+ATP+MgCl$_2$ (same preparation as experiment in example 2) and one with 5 microliter saline+ATP+MgCl$_2$. 24 hours and 1 week later, mice are sacrificed and both eyes are enucleated. Near infrared (NIR) spectra are recorded off-line using a NIR spectrometer equipped with an immobilized reflection probe of seven 400 μm fibers, an InGaAs detector and a halogen lamp (AvaSpecNIR256-2.5-HSC with an FCR-7UVIR400-2-BX reflection probe, Avantes). As glycation results in a spectral shift in the near-infrared spectrum of proteins, it is possible to observe specific peak sharpening and spectral variations in NIR spectra due to deglycation of proteins. This allows us to distinguish fructosamine-3-kinase-treated from untreated eyes. The use of non-invasive NIR monitoring enables us to assess the treatment in a non-destructive way.

Example 4. Treatment of Drüsen in Human Cadaver Eyes by Intravitreal Injection Human cadaver eyes (rejected for cornea transplantation) were transported on ice and evaluated for the presence of Drüsen by Optical Coherence Tomography within 24 hours after prelevation. When Drüsen were present, the Drüsen were treated by intravitreal injection into the eye with FN3K+ATP+MgCl$_2$+0.1 mol/L thiosulfate+5 U/ml hyaluronidase. Thiosulfate was added to the mixture before intravitreal injection for optimal penetration of the calcium hydroxyapatite around large subretinal Drüsen. Hyaluronidase was added to the mixture for optimal penetration of the vitreous. Eyes were kept at 37° C. for 2 hours and Drüsen were again recorded by Optical Coherence Tomography (FIG. 6). In the four cadaver eyes where Drüsen were present, intravitreal injection with FN3K+ATP+MgCl$_2$ induces a clear reduction in size.

Example 5. FN3K Treatment of AGE-Modified Pig Retina In Vitro

Pig retinas were dissected within 24 hours after prelevation. UV-fluorescence spectroscopy of AGES in pig retina was performed at baseline and after treatment with two of the most prevalent AGEs in human retina (methylglyoxal (MG), glycolaldehyde (GA) for 24 hours. Pig retinas were then washed with PBS and treated with saline+Mg Cl$_2$+ATP or with FN3K+Mg Cl$_2$+ATP for 24 hours, and UV-fluorescence spectroscopy was repeated.

TABLE 2

Norm. fluorescence intensities (a.u.) of neural pig retinas at baseline, AGE-modification and after control and FN3K treatment.

| | MG-AGEs | | GA-AGEs | |
|---|---|---|---|---|
| | Control (n = 30) | FN3K (n = 30) | Control (n = 30) | FN3K (control = 30) |
| Baseline | | | | |
| 440 nm | 5.6 (5.2-6.0) | 6.6 (6.1-6.9) | 6.4 (6.1-6.9) | 6.7 (5.9-6.9) |
| 490 nm | 7.1 (6.5-7.4) | 7.9 (7.1-8.5) | 7.9 (7.3-8.4) | 8.5 (8.0-91) |
| 490/440 nm | 1.3 (1.1-1.4) | 1.2 (1.1-1.3) | 1.2 (1.1-1.3) | 1.3 (1.2-1.4) |
| AGE-modification | | | | |
| 440 nm | 26.2 (19.4-40.6) | 30.6 (22.3-43.0) | 31.2 (26.2-50.2) | 23.7 (20.4-28.9) |
| 490 nm | 28.8 (22.1-49.6) | 34.2 (23.6-53.0) | 55.3 (47.5-96.0) | 39.3 (31.2-46.3) |
| 490/440 nm | 1.1 (1.1-1.2) | 1.2 (1.1-1.2) | 1.8 (1.8-1.9) | 1.6 (1.5-1.7) |
| Treatment | | | | |
| 440 nm | 32.5 (19.8-44.7) | 22.5 (18.0-26.4) | 25.1 (23.5-32.7) | 16.2 (11.0-20.0) |
| 490 nm | 35.8 (19.3-50.3) | 23.4 (18.0-26.4) | 40.8 (36.9-58.6) | 19.4 (13.6-28.2) |
| 490/440 nm | 1.1 (1.0-1.1) | 1.1 (1.0-1.1) | 1.6 (1.6-1.8) | 1.3 (1.2-1.4) |
| Baseline vs AGE-modification (P-value) | | | | |
| 440 nm | <0.0001 | <0.0001 | <0.0001 | <0.0001 |
| 490 nm | <0.0001 | <0.0001 | <0.0001 | <0.0001 |
| 490/440 nm | <0.01 | 0.06 | <0.0001 | <0.0001 |
| AGE-modification vs Treatment (P-value) | | | | |
| 440 nm | N.S. | <0.05 | <0.05 | 0.0001 |
| 490 nm | N.S. | <0.01 | <0.001 | <0.0001 |
| 490/440 nm | <0.05 | <0.001 | <0.0001 | <0.0001 |

Six porcine eyes were obtained from a local abattoir and stored at 4° C. until processing. Neural retinas were isolated through dissection by a trained ophthalmologist within 12 h post-mortem, transferred to a sterile 6-well plate (Thermo scientific, Roskilde, Denmark) and stored at 4° C. in RPMI-1640 medium (Sigma-Aldrich, St. Louis, Missouri, USA). The experiment was started within 48 h by removing the RPMI medium and carefully washing the retinas five times with 5 mL phosphate buffered saline (PBS) solution. Subsequently, maillard type fluorescence measurements (excitation 370 nm, emission 390-700 nm) were performed at baseline on each retina (30 different measurement locations) using a miniature spectrometer system (Flame-S—VIS-NIR, Ocean Optics, Largo, Fla.) at fixed distance and 90° angle. AGE modification was performed by incubation of two retina wells with 4 mL 100 mmol/L methylglyoxal (methyl glyoxal solution ~40% in H$_2$O, Sigma-Aldrich), and two with 4 mL 100 mmol/L glycolaldehyde dimer (crystalline form, Sigma-Aldrich) in phosphate buffered saline (PBS) for 24 h at 37° C. After incubation, the active agents were carefully washed away (10 times) in each well with 5 mL PBS and fluorescence measurements were performed again. Finally, in vitro deglycation was initiated using ATP-dependent FN3K (Fitzgerald Industries International, Acton, MA, USA). A solution containing 0.0016 g/L ATP-dependent FN3K in PBS was added (1:1) to a mixture of 5 mmol/L ATP and 2 mmol/L MgCl$_2$ (Sigma-Aldrich) in PBS. Two milliliters of the final FN3K solution were added to one retina well incubated with methylglyoxal, and one with glycolaldehyde and incubated for 24 h at 37° C. The remaining wells were control treated with PBS. After the treatment procedure, all wells were washed five times with PBS and fluorescence measurements were performed.

FN3K treatment reduced fluorescence of intraretinal AGEs in pig retinas in vitro.

Example 6. Treatment of Eyes of Ob/Ob Mice and Wt Mice. In Vivo Experiment

Tests are carried out on aged ob/ob mice, which show the typical diabetic lesions. Following FN3K treatment in one eye by intravitreal injection, mice retinas are studied using near-infrared (NIR) and fluorescence spectroscopy.

Histological sections are performed to evaluate typical lesions in DR and DME, such as an increase in large leaky vessels and in thickness of collagen fibers in the inner limiting membrane. FIG. 7 shows signs of diabetic retinopathy in ob/ob mice treated with saline+ATP+$MgCl_2$ with large leaky vessels (large arrow), and a very thick collagenous inner limiting membrane (triangle). Retinas of ob/ob mice treated with FN3K+ATP+$MgCl_2$ showed normalization of the retina and normal microvasculature (small arrows) comparable with wt mice.

Mice from 30-36 weeks old are anesthetized during the surgical procedure with inhalation anesthesia (isoflurane 5%). Both eyes of the same animal are injected, one with 5 microliter fructosamine-3 kinase+ATP+$MgCl_2$ (same preparation as experiment in example 2) and one with 5 microliter saline+ATP+$MgCl_2$. 24 hours later, mice are sacrificed and both eyes are enucleated. Near infrared (NIR) spectra are recorded off-line using a NIR spectrometer equipped with an immobilized reflection probe of seven 400 µm fibers, an InGaAs detector and a halogen lamp (AvaSpecNIR256-2.5-HSC with an FCR-7UVIR400-2-BX reflection probe, Avantes). As glycation results in a spectral shift in the near-infrared spectrum of proteins, it is possible to observe specific peak sharpening and spectral variations in NIR spectra due to deglycation of proteins. This allows us to distinguish fructosamine-3-kinase-treated from untreated eyes. The use of non-invasive NIR monitoring enables us to assess the treatment in a non-destructive way.

Example 7. FN3K Treatment of AGEs in the Ciliary Body of Human Cadaver Eye In Vitro Ciliary body was dissected from human cadaver eyes (waste material rejected for corneal transplantation) and treated for 3 hours ex vivo with 3 mL FN3K (41.6 □g/mL)+ATP 2.5 mmol/L+MgCl2 (1 mmol/L). Fluorometry (FIG. 8) was performed after 1 hour, 2 hours and 3 hours of FN3K treatment using a miniature spectrometer system (Flame-S-VIS-NIR, Ocean Optics, Largo, Fla.) at fixed distance and 90° angle. QR400-7-VIS-BX Premium 400 micron reflection probe was used.

Example 8 Treatment of Human Cadaver Eyes by External Application of FN3K Drops Ex Vivo Human cadaver eyes (waste material rejected for corneal transplantation) were treated within 24 hours after prelevation. For cross over experiments, always two eyes from the same donor are used.

The technique of applying FN3K drops or saline drops to the intact human cadaver eye consists of the following: 6 to 7 drops of FN3K (25 □g/mL)+ATP (5 mmol/L)+MgCl2 (2 mmol/L) solution were applied every hour for 6 hours on one eye and saline drops were applied every hour for 6 hours on the other eye from the same donor. Fluorometry was performed at baseline before treatment and 6 hours after treatment using a miniature spectrometer system (Flame-S-VIS-NIR, Ocean Optics, Largo, Fla.) at fixed distance and 90° angle. QR400-7-VIS-BX Premium 400 micron reflection probe was used. First, one eye is treated with FN3K drops and the other eye of the same donor is treated with saline drops. For cross over experiments, treatment is then switched, and the FN3K treated eyes are further on treated with saline drops, while the eyes initially treated with FN3K are further on treated with saline drops for 6 hours. Fluorometry is performed at baseline (start experiment, t=0 hr), after 6 hours of initial treatment, and after 6 hours of the other treatment.

REFERENCES

1. Bejarano E and Taylor A. Too sweet: problems of protein glycation in the eye. Exp Eye Res 2019; 178:255-262.
2. Wong W L et al. Global prevalence of age-related macular degeneration and disease burden projection for 2020 and 2040: A systematic review and meta-analysis. Lancet Glob Health 2014; 2:e106-16.
3. Cheng W et al. Overview of clinical trials for dry age-related macular degeneration. J Med Sci 2017; 37:121-9.
4. Group UPDS. Risks of progression of retinopathy and vision loss related to tight blood pressure control in type 2 diabetes mellitus. UKPDS 69, Arch Ophthalmol 2004; 122, 1631. White N H et al. Beneficial effects of intensive therapy of diabetes during adolescence: outcomes after the conclusion of the Diabetes Control and Complications Trial (DCCT). J Pediat 2001; 139:804-812
5. Wang J et al. Photosensitization of A2E triggers telomere dysfunction and accelerates retinal pigment epithelium senescence. Cell Death and Disease 2018; 9:178.
6. Stitt A W. The Maillard Reaction in Eye Diseases Ann N Y Acad Sci 2005; 1043:582-97.
7. Hollyfield J et al. Proteomic approaches to understanding age-related macular degeneration. Adv Exp Med Biol 2003; 533:83-9.
8. Yamada Y et al. The expression of advanced glycation endproduct receptors in RPE cells associated with basal deposits in human maculas Exp Eye Res 2006; 82:840-8.
9. Bergen A A et al. On the origin of proteins in human drusen: The meet, greet and stick hypothesis. Prog Retin Eye Res 2019; 70:55-84.
10. Bogunovic H et al. Machine learning of the progression of intermediated age-related macular degeneration based on OCT imaging. Invest Ophthalmol Vis Sci 2017; 58:BIO141-BIO150.
11. Glenn J V and Stitt A W. The role of advanced glycation end products in retinal ageing and disease. Biochim Biophys Acta 2009; 1790:1109-16.
12. Yoon K D et al. A novel source of methylglyoxal and glyoxal in retina: implications for age-related macular degeneration. PLoS One 2012; 7:e41309.
13. Delpierre G, Collard F, Fortpied J, Van Schaftingen E. Fructosamine 3-kinase is involved in an intracellular deglycation pathway in human erythrocytes. Biochem J 2002; 365:801-8.
14. Rosenfeld P J, Brown D M, Heier J S, Boyer D S, Kaiser P K, Chung C Y, Kim R Y, for the MARINA Study Group. Ranibizumab for neovascular age-related macular degeneration. N Engl J Med 2006; 355:1419-31.
15. Halfter W, Dong S, Schurer B, Ring C, Cole G J, Eller A. Embryonic synthesis of the inner limiting membrane and vitreous body. Invest Ophthalmol Vis Sci 2005; 46:2202-9.

16. Delpierre G, Rider M H, Collard F, Stroobant V, Vanstapel H & Santos E (2000) Identification, cloning, and heterologous expression of a mammalian fructosamine-3-kinase. Diabetes 49: 1627-1634.
17. Szwergold B S, Howell S & Beisswenger P J (2001) Human fructosamine-3-kinase: purification, sequencing, substrate specificity, and evidence of activity in vivo. Diabetes 50: 2139-2147.
18. Ryan D. Woodyer, Tyler Johannes, and Huimin Zhao, "Regeneration of Cofactors for Enzyme Biocatalysis in Enzyme Technology," in Enzyme Technology (Springer Science+Business Media, Inc. and Asiatech Publishers, Inc., 2006).
19. Andexer J N & Richter M (2015) Emerging Enzymes for ATP Regeneration in Biocatalytic Processes. ChemBioChem 16: 380-386.

The invention claimed is:

1. A method of treating a subject for a condition selected from the group consisting of age-related macular degeneration, diabetic retinopathy, diabetic macular edema, and a combination of any thereof,
wherein the subject is a human or an animal having at least one eye, and
wherein the subject has accumulated advance glycation end products (AGEs) in the eye(s),
the method comprising:
administering to the subject's eye(s) a composition comprising a fructosamine-3-kinase and adenosine triphosphate (ATP)
so as to reduce the accumulated AGEs in the subject's eye(s) and thereby treat the subject for the condition.

2. The method according to claim 1, wherein the composition is administered by intravitreal injection.

3. The method according to claim 1, wherein the composition further comprises magnesium ions.

4. The method according to claim 1, wherein the composition further comprises an ATP-generating system.

5. The method according to claim 1, wherein the fructosamine-3-kinase is a recombinant fructosamine-3-kinase.

6. The method according to claim 5, wherein the recombinant fructosamine-3-kinase is produced by recombinant production in *Pichia pastoris*.

7. The method according to claim 6, wherein the recombinant fructosamine-3-kinase has an amino acid sequence as given by SEQ ID NO: 1 or SEQ ID NO:2.

8. The method according to claim 1, wherein the subject has retinal or subretinal AGEs and fluorophores and the treatment results in a deglycation of the retinal or subretinal advanced glycation end products and fluorophores.

9. The method according to claim 1, wherein the composition further comprises 0.1 mol/L thiosulfate and 5 U/ml hyaluronidase when amounts greater than or equal to 5 µl per eye of the composition are administered to the subject.

10. The method according to claim 1, wherein the condition is age-related macular degeneration.

11. The method according to claim 10, which reduces Drüsen in the subject's eye(s).

12. The method according to claim 1, wherein the condition is diabetic retinopathy.

13. The method according to claim 1, wherein the condition is diabetic macular edema.

* * * * *